US006225132B1

(12) United States Patent
Drukier et al.

(10) Patent No.: US 6,225,132 B1
(45) Date of Patent: May 1, 2001

(54) ENHANCED CHROMATOGRAPHY USING MULTIPHOTON DETECTION

(75) Inventors: Andrzej K. Drukier, Burke, VA (US); Roman Bielski, Coopersburg, PA (US)

(73) Assignee: BioTraces, Inc., Fairfax, VA (US)

( * ) Notice: Subject to any disclaimer, the term of this patent is extended or adjusted under 35 U.S.C. 154(b) by 0 days.

(21) Appl. No.: 09/208,495

(22) Filed: Dec. 10, 1998

Related U.S. Application Data

(63) Continuation of application No. 08/679,671, filed on Jul. 12, 1996, now Pat. No. 5,854,084, and a continuation-in-part of application No. 08/669,970, filed on Jun. 25, 1996, now Pat. No. 5,866,907, which is a continuation-in-part of application No. 08/133,919, filed on Oct. 12, 1993, now Pat. No. 5,532,122.
(60) Provisional application No. 60/001,129, filed on Jul. 13, 1995.

(51) Int. Cl.[7] .................... G01N 33/533; G01N 21/76; G01N 33/532; G01N 33/536
(52) U.S. Cl. .................. 436/541; 436/538; 436/545; 436/161; 436/162; 436/804; 436/501; 436/544; 436/546; 436/50; 436/56; 436/172; 435/7.1; 435/7.8; 435/7.93; 435/7.94; 435/7.95; 435/8; 435/807; 73/19.02; 73/23.22; 73/61.52
(58) Field of Search ..................... 435/4, 5, 7, 7.1, 435/7.8, 7.93, 7.94, 7.95, 807, 6, 7.2, 7.22, 7.23, 7.31, 7.32, 7.36; 436/538, 541, 545, 161, 162, 804, 57, 504, 542, 807; 250/303

(56) References Cited

U.S. PATENT DOCUMENTS

| | | |
|---|---|---|
| 3,924,125 | 12/1975 | Murray . |
| 3,974,088 | 8/1976 | Coffey . |
| 3,979,593 | 9/1976 | Spragg et al. . |
| 4,005,292 | 1/1977 | Oesterlin et al. . |
| 4,016,418 | 4/1977 | Horrocks et al. . |
| 4,395,634 | 7/1983 | Bohme . |
| 4,444,744 | 4/1984 | Goldenberg . |
| 4,495,420 | 1/1985 | Chudy et al. . |
| 4,563,419 | 1/1986 | Ranki et al. . |
| 4,604,364 * | 8/1986 | Kosak ................................ 436/501 |
| 4,651,006 | 3/1987 | Valenta . |
| 4,682,604 | 7/1987 | Fymat et al. . |
| 4,683,195 | 7/1987 | Mullis et al. . |
| 4,864,140 | 9/1989 | Rogers et al. . |
| 4,931,646 | 6/1990 | Koechner et al. . |
| 4,983,841 | 1/1991 | Stewart et al. . |
| 4,990,785 | 2/1991 | Logan . |
| 5,016,009 | 5/1991 | Whiting et al. . |
| 5,083,026 | 1/1992 | Elbaum . |
| 5,146,093 | 9/1992 | Valenta et al. . |
| 5,285,073 | 2/1994 | Schelten et al. . |
| 5,532,122 * | 7/1996 | Drukier ................................ 435/5 |
| 5,854,084 * | 12/1998 | Drukier et al. ..................... 436/541 |

FOREIGN PATENT DOCUMENTS 241788   12/1986   (DE) .

OTHER PUBLICATIONS

Odell and Daughaday., "Principles of competitive protein–binding assays.", Published by J.B. Lippincott Company, Philadelphia and Toronto, Copyright 1971, pp. 134–152, 1980.*
Gosling, James P., Clinical Chemistry, 36/8, 1408–1427, 1990.*
Sack et al., Analytical Chemistry, 57, 1290–1295, 1985.*
Voet et al., Biochemistry, Second Edition, 71–103, 1995.*
G. Faraci, et al., "*Simultaneous Counting of True and Random Events in a Four–Fold Coincidence System Using Two Time–To–Pulse–Height Converters*," Nuclear Instruments & Methods in Physics Research, vol. 164, No. 1, (1979), pp. 157–162.
Yu A. Novikov, "*Universal Coincidence Circuit*," Instruments and Experimental Techniques, vol. 25, No. 6, (1982), pp. 1386–1389.
Avignone, et al., "*Search for the Double–B Decay of Germanium–76*," The American Physical Society, vol. 34, No. 2, (1986), pp. 666–677.
Brodzinski, et al., "*Achieving Ultralow Background in a Germanium Spectrometer*," Journal of Radioanalyticla and Nuclear Chemistry Articles, vol. 124, No. 2, (1988), pp. 513–521.
Brodzinski, et al., "*The Impact of Natural Radioactivity in Solder on Low Background Experiments*," Nuclear Instruments and Methods in Physics Research A254, (1987), pp. 472–473.
J.A.D.M. Tonnaer, "*Angiotensins*," Handbook of HPLC for Separation of Amino Acids, Peptides and Proteins, vol. II, (1984) pp. 179–.

(List continued on next page.)

*Primary Examiner*—Long V. Le
*Assistant Examiner*—Lisa V. Cook
(74) *Attorney, Agent, or Firm*—Venable; Michael A. Gollin

(57) ABSTRACT

A method for detecting an analyte of interest present in a mixture at an ultralow concentration includes selecting a radioactive derivatizing agent comprising a multiphoton-emitting radioisotope moiety and a moiety reactive with the analyte of interest, the radioisotope moeity being bound to the derivatizing agent by a bond that is stable under the conditions employed in the other steps of the method, derivatizing the analyte of interest with the derivatizing agent, separating the analyte of interest from other components of the mixture by chromatography, and detecting the analyte of interest using multiphoton detection. The derivatizing step may be performed before or after fractionation. A radiophore for multiphoton emission enhanced chromatography has a first moeity bound to a multiphoton-emitting radioisotope, and a second moiety that is reactive with a functional group of an analyte of interest. The first moiety may be a benzene group having an alkoxy, amino, or thiol group, bound to a halogen radioisotope; a complexing agent able to form a stable complex with a metal radioisotope such as a lanthanide or heavy metal.

45 Claims, 10 Drawing Sheets

OTHER PUBLICATIONS

W.H. Church, et al., "*On–Line Small–Bore Chromatography for Neurochemical Analysis in the Brain*," Advance in Chromatography, Marcel Dekker, Inc., vol. 28, (1989), pp. 165–194.

P.R. Fielden et al., "*Recent Developments in LC Detector Technology*," J. Chrom. Science, (1992), vol. 30, p.

M.E.P. McNally, A.C. Barefoot III, "*Chromatography: Future Directions In The Industrial Laboratory*," American Laboratory, (1994), pp. 28N–28W.

R. Stevenson, "*A Critical Review Of The Development of HPCE Instrumentation*," American Laboratory, (1994) pp. 29–33.

B. Willis, "*Analytical Chemistry Instrumentation and Systems: A View To The Future*," American Laboratory, (1994), pp. 13–17.

F.F. Hsu et al., "*Determination of Cortisol in Human Plasma by Gas Chromatography/Negative Ion Chemical Ionization/Mass Spectrometry*," Anal. Biochem., (1994), vol. 216, pp. 401–405.

C.A. Bruckner et al., "*Column Liquid Chromatography: Equipment and Instrumentation*," Anal. Chem., (1994) vol. 66, No. 12, pp. 1R–16R.

J.G. Dorsey et al., "*Liquid Chromatography: Theory and Methodology*," Anal. Chem., (1994), vol. 66, No. 12 pp. 500R–546R.

C. Steuckart et al., "*Determination of Explosives and Their Biodegradation Products in Contaminated Soil and Water From Former Ammunition Plants by Automated Multiple Development High–Performance Thin–Layer Chromatography*," Anal. Chem., (1994), vol. 66, No. 15, pp. 2570–2577.

H. Tabei et al., "*Subfemtomole Detection of Catecholamine with Interdigitated Array Carbon Microelectrodes in HPLC*," Anal. Chem., (1994), vol. 66, No. 20, pp. 3500–3502.

J. Fiet et al., "*Hirsutism and Acne in Women: Coordinated Radioimmunoassays for Eight Relevant Plasma Steroids*," Clin. Chem., (1994), vol. 40, No. 12, pp. 2296–2305.

J.R. Voelker et al., "*Improved HPLC–Radioimmunoassay for Quantifying Angiotensin II in Plasma*," Clin. Chen (1994), vol. 40, No. 8, pp. 1537–1543.

C. Holmes et al., "*Improved Assay For Plasma Dihydroxyphenylacetic Acid and Other Catechols Using High–Performance Liquid Chromatography With Electrochemical Detection*," J. Chromatography, B, (1994), vol. 653, pp. 131–138.

Y. Ohkura et al., "*Fluorogenic Reactions For Biomedical Chromatography*," J. Chromatography, B, (1994), vol. 659, pp. 85–107.

M.E. Bovingdon et al., "*Derivatization Reactions For Neurotransmitters and Their Automation*," J. Chromatography, B, (1994), vol. 659, pp. 157–183.

H. Gleispach et al., "*Applications of Gas Chromatography–mass Spectrometry in Clinical Chemistry*," J. Chromatography, A, (1994), vol. 665, pp. 155–162.

C. Legrand et al., "*Measurement of Plasma Testosterone by Gas Chromatography–Negative–Ion Mass Spectrometry Using Pentafluoropropion Derivatives,* " J. Chromatography, B, (1995), vol. 663, pp. 187–192.

S. Torres Cartas et al., "*Determination of Anabolic Steroids in Pharmaceuticals By Liquid Chromatography With Microemulsion of Sodium Dodecyl Sulfate and Pentanol as Mobile Phase*," Analytica Chimica Acta 302, (1995), pp. 163–172.

R.P.W. Scott, "*Modern Liquid Chromatography*," Chemical Society Reviews, 1992; pp. 137–145.

C.P. Martucci et al., "*P450 Enzymes of Estrogen Metabolism*," Pharmac. Ther., (1993), vol. 57, pp. 237–257.

S. A. Rossi et al., "*Short–Column Gas Chromatography/ Tandem Mass Spectrometry for the Detection of Underivatized Anabolic Steriods in Urine*," Biological Mass Spectrometry, (1994), vol. 23, pp. 131–139.

\* cited by examiner

ENHANCED CHROMATOGRAPHY USING MULTIPHOTON DETECTION

This application is a continuation of commonly-owned patent application Ser. No. 08/679,671, filed Jul. 12, 1996, now U.S. Pat. No. 5,854,084 which is entitled to the priority of provisional patent application No. 60/001,129, filed Jul. 13, 1995, and this application is a continuation-in-part of patent application Ser. No. 08/669,970, filed Jun. 25, 1996, now U.S. Pat No. 5,866,907 which is a continuation-in-part of patent application Ser. No. 08/133,919, filed Oct. 12, 1993, now U.S. Pat. No. 5,532,122.

This application is related to commonly owned U.S. Pat. No. 5,532,122, issued Jul. 2, 1996, and to a commonly owned application filed Jun. 25, 1996 entitled "Ultralow Background Multiple Photon Detector," the disclosures of all of which are incorporated herein by reference.

BACKGROUND OF THE INVENTION

1. Field of the Invention

The invention provides chromatographic methods and reagents suitable for the detection and quantification of analytes of interest at femtomolar ($10^{-15}$ M) concentrations. More specifically, the invention relates to binding a radioactive derivatizing agent to an analyte of interest present in a mixture at low concentration, separating the analyte of interest, and detecting it using multiphoton detection.

2. Background Information

The separation and detection of minute concentrations of chemicals in gas, liquid and solid environments is important in many applications, such as environmental diagnostics, biomedical applications and materials processing, particularly in the chemical and petroleum industries. Sensitive albeit inconvenient methods of measuring separation products have been developed, including mass spectroscopy (MS) and neutron activation for chemical applications, and fluorescence, luminescence, color spectroscopy and radiographic detectors for biomedical applications. Scientists continue to push detection sensitivity to lower and lower chemical concentrations. A few decades ago the operative term was microtraces. Today, femtotraces, i.e. materials present in sub-femtogram ($10^{-15}$ g) quantities, are of interest.

Chromatography is the method of choice when the detection and quantitation of specific compound(s) within mixture are needed, especially if the mixture contains several compounds with relatively similar structure. High Performance Liquid Chromatography (HPLC), Thin Layer Chromatography (TLC), Gas Chromatography (GC) and Capillary Electrophoresis (CE) have emerged as the preferred separation methods for a wide variety of applications due to their excellent sensitivity, selectivity, reproducibility and convenience of use.

Recent reviews on chromatography and detectors in use are provided in R.P.W. Scott, "Chemical Society Reviews," *Modern Liquid Chromatography*, (June 1992); P. R. Fielden et al., "Developments in LC Detector Technology," *J. Chrom. Science*, 30, 1992; C. A. Bruckner et al., "Column Liquid Chromatography: Equipment and Instrumentation," *Anal. Chem.*, 66, 1R, 1994; and J. G. Dorsey et al., "Liquid Chromatography: Theory and Methodology," *Anal. Chem.*, 66, 500R, 1994. With recent broadening of chromatography applications, in many important cases chromatographic techniques are limited by the sensitivity of existing methods of detection. R. Stevenson, "A critical review of the development of HPCE instrumentation," *American Laboratory*, Dec. 1994, pp. 29–33; M. E. McNally, A. C. Barefoot III; "Chromatography: Future directions in the industrial systems," *American Laboratory*, Dec. 1994 pp. 28N–28W; W. Willis, "Analytical chemistry instrumentation and systems: A view to the future", *American Laboratory*, Dec. 1994 pp. 13–17.

There is an acute need for more sensitive detection, identification and quantification of analytes separated by chromatography. Better understanding of different mechanisms calls for the study of constituent materials which are present in increasingly lower concentrations. Recently, applications appeared wherein the materials are available in picogram quantities, and sub-femtogram fractionation outputs are of interest.

Fractions leaving an HPLC column are typically quantitated by electrochemical or UV absorption detectors. This applies particularly to mixtures containing very small amounts of material. When using HPLC there is a tradeoff between sensitivity and specificity. Often, the column separation process is preceded by some pre-purification step which employs alumina, solid-phase extraction or liquid-liquid extraction to remove undesired components of the mixture, which enables better specificity of the chromatography. Pre-purification, however, often causes relatively low recoveries of some reactants. In recent years there have been attempts to improve the sensitivity of detection by employing small-bore columns (i.d. <2.0 mm). One important advantage of the microbore columns is that very small samples may be analyzed. C. P. Martucci et al., *Pharmacol. Ther.* 57 (2–3), 237, 1993; F. F. Hsu et al., *Analyt. Biochem.*, 216, 401, 1994.

To introduce properties compatible with a particular detector and mixture components, derivatizing agents are sometimes used. Derivatized mixtures may be separated better than non-reacted components. Pre-column derivatization is more often used than the post-column process. The chemistry of these derivatizing agents can be very diverse (see review in R. Yost et al., *Biol. Mass. Spectrom.*, 23, 131, 1994).

Currently, the most sensitive detection methods used in chromatography are mass-spectroscopy (MS), UV detection (UVD), electrochemical detection (ECD) and laser induced fluorescence (LIF). MS is typically used with gas chromatography whereas UVD and ECD are most useful for liquid chromatography. Furthermore, radiolabeling methods based on tritium and $C^{14}$ are often used, especially in thin layer chromatography.

Detectors currently used with chromatography respond to solute concentrations over the range of about $10^{-7}$ to $10^{-12}$ g/ml. The following Table shows the present practical limits of the most popular chromatographic detection methods.

| UV-VIS | Fluorescence | Refractive Index | Electro-chemical | Conductivity |
|---|---|---|---|---|
| $2 \times 10^{-10}$ g/ml | $10^{-11}$ g/ml | $10^{-7}$ g/ml | $10^{-12}$ g/ml | $10^{-8}$ g/ml |

Current HPLC detector sensitivity is typically around a picomole/ml ($10^{-12}$ mole/ml) and is rarely better than $10^{-14}$ mole/ml. This corresponds to nanomolar to picomolar concentrations. It would be extremely desirable to obtain a sensitivity of three orders of magnitude higher, that is, to femtomolar concentrations.

Absorbance Detectors

UV-VIS absorbance detectors are very popular in HPLC and CE since they are relatively inexpensive and can be focused down to the dimensions of the column or capillary. Also, most compounds of interest have UV-absorbing chromophores. The few that do not, such as common anions and small molecules, are candidates for indirect detection. The principal problem with absorbance detection in HPLC is that the path length of the cell is only as wide as the column, which is only a few millimeters. This limits the retention time within the detector. Recently, a special UVD for HPLC was designed where one looks down a long vertical segment. This improves detection by about a factor of 50. In some detectors, a bubble is induced in the flow cell to increase the path length and decrease the apparent peak width. With all of these improvements, however, detection limits are still in the range of $10^{-7}$ mole/ml. The noise levels of these detectors are already very low and probably will continue to improve by not more than a factor of a few per decade. In TLC, the UVD performance is further limited by light absorption and scatter in the granulated medium.

Fluorescence Detection

Fluorescence detection offers the potential of improving detection limits by about a hundred times over UV absorbance. The detected intensity is function of the incident light and the quantum yield for the fluorophore group. It depends upon the performance of the light collection optics. The major requirement is that the excitation beam be isolated as much as possible from the emission optics in order to have the best possible signal-to-noise ratio. A variety of fluorescence detectors have been developed. One novel design uses a microscope to focus the excitation beam on the capillary and then collect the fluorescence signal through the same optics.

Fluorescence detectors with non-laser excitation sources are capable of detection limits in the $10^{-9}$ mole range. Lasers can increase the flux of excitation light, which extends detection limits to about $10^{-13}$ mole/ml in favorable cases. Stronger lasers might increase the LOD still further, but one quickly runs into problems of photo-bleaching and heating of the cell. Scattering from the cell wall can also be an important limitation on signal to noise.

Mass Spectrometer Detectors

GC-MS is a mature, popular but very expensive chromatographic modality. HPLC-MS is a technique that has only recently become practical due to the advent of interfaces such as thermospray and electrospray, etc. These interfaces often use splitters to reject most of the liquid from the HPLC column, which is typically flowing at 1 ml/min. With high performance capillary electrophoresis the problem is that the flow is often too low to provide rapid transit to the inlet of the mass spectrometer. The sensitivity can be improved by adding sheathed flow that provides both transport and electrical grounding. Detection limits are in the picomole range, and large molecules such as proteins, including immunoglobulins, can be studied. Pushing up the price tag even further, fast ion bombardment can provide LOD of about 50 fmole of peptides, but this is not yet commercially available.

Electrochemical Detectors

Conductivity detectors have been described with detection limits of about $10^{-7}$ mole/ml for the favorable case of $Li^+$. Conceivably, suppression techniques could improve the LOD a bit, but the entire system would need to be very small. Amperometric detection seems to be more promising for improved LOD. For example, A. Ewing et al., Pennsylvania State University, demonstrated that the capillary can be isolated from the high voltage required for separation by electrically isolating the section before the end by fracturing it or by inserting a section of porous polymer, glass, or carbon and grounding it. This approach improves sensitivity by about a factor of a hundred.

Single beta and gamma detection techniques have been used previously in both HPLC and TLC. Typically, the chromatogram is scanned by a radiation detector and the count rate is recorded as a function of source position, which permits the measurement of flow-through time. For this purpose, three different types of detectors have been used: the TLC scanner, the TLC linear detector, and 2 D spatially resolving detectors. Spatially resolving 2 D detectors previously used in chromatography include nuclear emulsions, gas chambers, liquid scintillation counters and CCD based detectors. The detection limit for classical autoradiographic methods is much larger than a million atoms of label. With overnight exposure, sources with activities of the order of 10 decays per minute (dpm) can be detected. The older radioisotope techniques used mostly beta emitters, which limits the applications to TLC. For example, with spatially resolving gas detectors spots containing typically 100 dpm of tritium or 20 dpm of $C^{14}$ on an area of a few $mm^2$ can be resolved with exposure times of about 15 minutes.

In the field of HPLC, the use of beta-emitters as labels and subsequent quantitation by liquid scintillator based techniques permits to match and even slightly improve upon the performance of the best UVD detectors. A detector for positron-gamma (PG) emitters is described in U.S. Pat. No. 5,083,026. The PG emitters include $I^{123}$.

SUMMARY OF THE INVENTION

Chromatography enhanced by multiphoton detection according to the invention is up to four orders of magnitude more sensitive than previous techniques using radioisotopes for quantitation of chromatography outputs. Chromatographic methods and reagents according to the invention are suitable for the detection and quantification of an analyte of interest present in a mixture at ultralow concentrations, such as one attomole per ml (one femtomolar, or $10^{-15}$ M), or less than one part per trillion, and in some cases below one part per quadrillion.

This invention is in the crowded and mature art of chromatography, and succeeds where previous efforts to obtain enhanced chromatography have failed. This invention also solves the previously unrecognized problem of using reagents containing picoCurie quantities of multiphoton emitters to label analytes of interest.

Further objectives and advantages will become apparent from a consideration of the description and drawings.

The method of the invention comprises the steps, without regard to order, of providing a radiophore, meaning a radioactive derivatizing agent comprising a multiphoton-emitting radioisotope moiety and a moiety reactive with the analyte of interest, the radioisotope moiety being bound to the derivatizing agent by a bond that is stable under the conditions employed in the other steps of the method; derivatizing the analyte of interest with the derivatizing agent; separating the analyte of interest from other components of the mixture by chromatography; and detecting the analyte of interest using multiphoton detection.

Derivatization with the radiophore may be performed before, during, or after fractionation. If derivatizing is done post-fractionation, it is necessary to remove excess non-reacted derivatizing agent prior to detection, for example by means of a solid phase reagent that binds non-reacted derivatizing agent and can be filtered away from the analyte of interest.

The radioactive moeity of the derivatizing agent is a multiphoton detection-compatible radioisotope, preferably a radioisotope of iodine, another electron capture emitter, or a positron-gamma emitter. The radioisotope is bound to the derivatizing agent to produce a radioactive derivatizing agent, preferably prior to derivatization of the analyte of interest. The radioisotope-derivatizing agent bond is stable under anticipated reaction conditions, and is preferably covalent. In a preferred embodiment, the radioactive derivatizing agent is an aromatic compound in which radioiodine is bound to the benzene moeity of an aromatic compound, the benzene ring having increased electron density, such as a methoxybenzyl or hydroxybenzyl moeity. The radioiodo-derivatizing agent may be synthesized from a suitable starting material by electrophilic aromatic substitution. Alternatively, a radioiodo-derivatizing agent may be synthesized from a halogenated derivatizing agent by nucleophilic aromatic substitution whereby the non-radioactive halogen (e.g. bromine) is replaced by radioactive iodine. This reaction is less hazardous in that it is less likely to release elemental radioiodine into the environment.

The derivatizing agent is preferably one that reacts to form a covalent bond with the analyte of interest. The derivatizing agent is selected depending on the class of compound to be derivatized. Covalent bonding is preferred because it allows derivatization to occur expeditiously despite the kinetics of very low concentrations of analyte and radiophore. Non-covalent bonding such as chelation and hydrogen bonding is possible with certain very high affinity derivatizing agents, which are able to bind with the analyte of interest at subfemtomole concentrations of the analyte of interest within a technically practical period of time (e.g. within hours, preferably within minutes or seconds).

It is also beneficial to minimize the amount of radioisotope employed, both in preparing the radioderivatizing agent, and in reacting the radioderivatizing agent with the analyte of interest, so that the practitioner does not exceed the exempt amounts for radioisotopes stipulated by the Nuclear Regulatory Commission at 10 Code of Federal Regulations, Part 30. For $I^{125}$, the exempt amount is no greater than 1 microCi. Therefore, if one can use less than one nanoCi per reaction, one can run more than 1000 reactions with the exempt amount of radioisotope. This is in contrast to the microCi quantities of radioisotope required for conventional detection (other than ultralow background multiphoton detection). Thus, the methods and reagents of the invention provide the advantage of avoiding the need to use regulated quantities of radioisotopes.

Chromatography according to the invention comprises any technique for separating components of a mixture involving differential migration of the components through a medium, based on the physical-chemical characteristics of the components. Thus, chromatography includes liquid chromatography (LC), thin layer chromatography (TLC), gas chromatography (GC), ion exchange chromatography (IEC), capillary electrophoresis (CE), high performance liquid chromatography (HPLC), gel electrophoresis, affinity chromatography, and other methods known in the art. The analytes may be quantitated on-line during chromatographic separation.

Preferably, separation is stopped before quantitation. For example, the fractions are collected after chromatographic separation using a fraction collector and are then quantitated off-line by a single sample multiphoton detection device. If fractions are collected in a one dimensional blot strip, scanning techniques may hasten measurement. If fractions are collected in a two dimensional matrix, then spatially resolving detection techniques may be used, so that the sample throughput for the detection step is comparable to or less than the chromatography throughput rate. Chromatography may be stopped after partial separation, prior to elution of the analyte of interest, by stopping solvent flow or switching to a non-desorbing solvent, and the chromatographic medium (e.g. an HPLC column) may then be scanned by a multiphoton detection device.

The fractions may be deposited upon, absorbed upon, or adsorbed on an appropriate substrate to generate an essentially one dimensional (1 D) chromatogram, which is then quantitated by a scanning multiphoton detection device, or to generate an essentially two dimensional (2 D) chromatogram, which is then quantitated by a spatially resolving multiphoton detection device. The chromatogram can be obtained by passing the analytes through an appropriate membrane, such as filter paper. The 2 D chromatogram can be reproducibly obtained by a mechanical raster scan of the output of HPLC or GC over the appropriate thin surface, and the dot blot pattern can be well defined geometrically, i.e. without diffusion of analyte between the dots.

The analytes may be conjugated to form appropriate compounds containing multiphoton emitter before the chromatographic step. The radioemitters may belong to the family of electron capture (EC) emitters and/or positron-gamma (pg) radio-emitters, preferably in the family of halogens, including bromines and iodines. The isotopes may be $Br^{76}$(16.5 h), $Br^{77}$(2.6 d); $I^{123}$(10 h), $I^{124}$(4.2 d), $I^{125}$(60 d), $I^{126}$(13.2 d).

The radioisotopes may belong to the family of lanthanides, including $La^{135}$ (19.8 h); $Ce^{133}$(6.3 h), $Ce^{134}$(3.0 d), $Ce^{135}$(22.0 h), $Ce^{137}$( 9.0 h), $Ce^{139}$(140 d); $Nd^{140}$(3.3 d); $Pm^{143}$(265 d), $Pm^{144}$ (440 d), $Pm^{145}$(18 y), $Pm^{146}$ (710 d), $Pm^{158m}$(40.6 d); $Sm^{145}$(340 d); $Eu^{145}$(5.6d), $Eu^{146m}$(1.58 d), $Eu^{146}$(4.6 d), $Eu^{147}$(24 d), $Eu^{148}$(54 d), $Eu^{149}$(120 d), $Eu^{150m}$(14 h), $Eu^{150}$(5 y), $Eu^{152}$(13 y); $Gd^{146}$ (48 d), $Gd^{147}$(35 h), $Gd^{149}$(9 d), $Gd^{151}$(120 d), $Gd^{153}$(200 d); $Tb^{151}$(19 h), $Tb^{152}$(18 h), $Tb^{153}$(2.58 d), $Tb^{154m}$(8 h), $Tb^{154}$ (21 h), $Tb^{165}$(5.4 d), $Tb^{160}$(73 d); $Dy^{155}$(10 h), $Dy^{157}$(8.2 h); $Tm^{165}$(1.21 d), $Tm^{167}$(9.6 d), $Tm^{168}$(85 d); $Yb^{169}$(32 d); $Lu^{169}$(1.5 d), $Lu^{170}$(2.0 d), $Lu^{171}$(8.3 d), $Lu^{172}$(6.7 d), $Lu^{173}$ (1.3 y), $Lu^{174m}$(165 d); $Hf^{173}$(24 h), $Hf^{175}$(70 d); $Ta^{175}$(11 h), $Ta^{176}$(8.0 h), $Ta^{177}$(2.21 d), $Ta^{179}$(1.6 y), $Ta^{180m}$(8.1 h).

The multiphoton emitters may belong to families of heavy metals and actinides, including $W^{181}$(130 d); $Re^{181}$(20 h), $Re^{182m}$(13 h), $Re^{182}$(64 h) $Re^{183}$(71 d), $Re^{184m}$(2.2 d), $Re^{184}$(50 d), $Re^{186}$(90 h); $Os^{183m}$(10 h), $Os^{183}$(12 h), $Os^{185}$ (94 d); $Ir^{185}$(15 h), $Ir^{187}$(12 h), $Ir^{188}$(1.71 d), $Ir^{189}$(11 d), $Ir^{190}$(11 d), $Ir^{192}$(74 d); $Pt^{191}$(3.0 d); $Au^{193}$(15.8 h), $Au^{194}$(39 h), $Au^{195}$ (200 d), $Au^{196}$(5.55 d); $Hg^{193m}$(1.1 d), $Hg^{193}$(6 h), $Hg^{194}$(130 d), $Hg^{195}$(1.66 d), $Hg^{195}$(9.5 h), $Hg^{197m}$(24 h), $Hg^{197}$(2.71 d); $Tl^{200}$(1.08 d), $Tl^{201}$(3.04 d), $Tl^{202}$(12 d), $Tl^{204}$(3.9 y); $Pb^{200}$(21 h), $Pb^{201}$(9.4 h), $Pb^{202}$(2.17 d); $Bi^{203}$ (12.3 h), $Bi^{204}$(11.6 h), $Bi^{206m}$(15.3 d), $Bi^{206}$(6.3 d), $Bi^{207}$ (30 y); $Po^{206}$(8.8 d); $At^{210}$(8.3 h), $At^{211}$(7.2 h); $Rn^{211}$(16 h), $Ac^{226}$(29 h); $Pa^{228}$(22 h), $Pa^{229}$(1.5 d) $U^{231}$(4.2 d); $Np^{234}$ (4.4 d); $Pu^{234}$(9 h), $Pu^{237}$(45.6 d); $Am^{239}$(12 h); $Cm^{241}$(35 d); $Bk^{245}$(4.95 d), $Bk^{246}$(1.8 d).

The analyzed mixture may be pre-column derivatized with a derivatizing agent containing an multiphoton detection compatible isotope. The derivatizing agent preferably contains, i.e. is bonded or complexed to, a radioisotope selected from the group of radioiodine ($^{123}I$, $^{124}I$, $^{125}I$, and $^{126}I$) isotopes. The derivatizing agent may contain, i.e. is bonded or complexed to, a radioisotope selected from the lanthanide series, the heavy metal series, or the actinide series.

The analyzed mixture may instead be post-column derivatized with a derivatizing agent containing radioisotope selected from the group of radioisotopes which are multiphoton detection compatible. Derivatizing agents containing multiphoton emitting radioisotopes may be used to introduce radioactive properties into the mixtures separated by chromatography.

The derivatizing agents may contain two or more multiphoton detection compatible radioactive atoms in one molecule, providing amplification of the signal which can be used to further increase the sensitivity of multiphoton detection enhanced chromatography.

Multiple color analysis may be performed with radioisotopes applied via multiple derivatizing agents reactive with different functional groups of the analyte of interest.

The functionality of the derivatizing agent may be such as to form amides with amines; carbamates or thiocarbamates with amines; substituted isoindole with amino groups in the presence of appropriate thiols; esters with alcohols; phenylhydrazones or sulfonyl hydrazones with aldehydes and ketones; substituted oxazoles with catechols and catecholamines.

Separation, detection, and quantitation of analytes by chromatography according to the invention may be applied to in vitro metabolic studies; to mixtures containing steroids such as anabolic steroids; to environmental diagnostics involving mixtures containing pesticides; to mixtures containing crown ethers, cryptands and similar complexing agents, and wherein the detection by the multiphoton detection method is preceded with treatment of samples with salts of $^{125}I$ iodide anion; to biomedical diagnostics using body fluids and tissues as samples; and to pharmaceutical quality control; to in vivo studies of the uptake and metabolism of organic compounds labeled with multiphoton emitting radioactive atoms, to protein and peptides such as angiotensins; and to saccharides.

Chromatographic separation may be applied to mixtures containing anions or cations. The separated mixture can consist of various cations such as Co, Ni, Fe (II), Cd, Mn, Cu, Pb, Zn and the post-column derivatizing agent may be radio-iodinated (4-(2-pyridylazo)resorcinol).

The separated mixture may consist of different nitro compounds which are first reduced and then chromatographed with pre- or post-column derivatization using an appropriate radiophore such as $^{125}I$ pipsyl chloride and then quantitated using mnltiphoton detection. The nitro compounds may be constituents of explosives and the reduction may be followed by the steps of derivatization of the formed poly-amines, poly-hydrazines and poly-alcohols with an appropriate radiophore such as $^{125}I$ pipsyl chloride, chromatography and quantitation using multiphoton detection. The reduction of nitro compounds may be followed by the steps of chromatographic separation, post-column derivatization with the appropriate radiophore such as $^{125}I$ pipsyl chloride and quantitation using multiphoton detection.

The quantity of separated compound of interest may be measured by a competitive binding process which involves the addition of the radioactive (hot) equivalent of the non-radioactive (cold) component of the separated mixture, and involves the steps of:
- placing a known amount of the radioactive (hot) compound in those fractions after chromatographic separation where the compound of interest is expected to be present;
- treating the mixture of cold and hot compound with an appropriate reagent for the functionality present in the compound bonded to the solid phase (polymeric beads);
- washing the beads;
- measuring beads activity using multiphoton detection or alternatively quantitating the liquid phase.

Phase transfer catalysts such as crown ethers, cryptands, tetraalkylammonium salts, tetraalkylphosphonium salts and similar compounds may be used to dissolve radioactive iodide or other salts containing radio-elements compatible with multiphoton detection and thus label hydrocarbon mixtures such as crude oil, gasoline and other petrochemical products for later identification by multiphoton detection enhanced chromatography.

Terpenes, steroids and similar compounds containing appropriate functional groups may instead be introduced to different cargos such as petrochemical products or explosives to establish a unique chromatographic fingerprint of a given product which can be used to establish the origin of an unknown sample e.g. when the said samples are discarded, spilled, or stolen. The process may involve the steps of:
- creating a set of a few to few tens of individual compounds;
- adding pre-established unique signature combinations of the tagging compounds in very low concentrations to a bulk mixture to provide a tagged mixture;
- radio-derivatizing the compounds to produce derivatized tagging compounds;
- performing chromatography of the tagged mixture with multiphoton detection.

Chromatographic separation and quantitation using multiphoton detection may be applied to drugs of abuse with the steps of:
- chromatographically separating a sample suspected of containing drugs of abuse or their metabolites;
- derivatizing with appropriate radiolabeled derivatizing agent, such as pipsic acid (p-$^{125}I$-iodobenzenesulfonic acid) to detect amines as bases (amphetamines, cocaine and metabolites, opiates, phencyclidines), or p-$^{125}I$-iodobenzoyl chloride to detect hydroxyl functionality (cannabinoids);
- removing the excess derivatizing agents;
- detecting and quantitating using multiphoton detection.

Radio-iodobenzoyl chloride can serve as the derivatizing agent for amines and alcohols. The starting reactant may be non-radioactive ethyl bromobenzoate and the following steps are performed:
- reacting ethyl bromobenzoate in dry dioxane with hexamethylditin (or hexa-n-butylditin) in the presence of tetrakis (triphenylphosphine) palladium(0) to give the trimethyltin (tributyltin) derivative;
- treating trimethyltin (tributyltin) derivative with Na$^{125}I$ and Chloramine-T to give the desired radio-iodo product;
- performing chromatography of this radioactive ester, hydrolysis with lithium hydroxide in THF and reaction with thionyl chloride or phosphorus pentachloride to yield radio-iodobenzoyl chloride.

Radioactive pipsyl chloride may be used as a derivatizing agent for amines and alcohols. The starting reactant is p-aminobenzenesulfonic acid and the following steps are performed:
- dissolving sulfanilic acid in dioxane and reacting with nitrous acid prepared in situ from sodium nitrite and hydrochloric acid at temperature below 5° C. to produce diazonium salt;
- submitting the diazonium salt to modified Sandmeyer reaction conditions i.e. to reaction with sodium iodide ($^{125}$INa) in the presence of powdered copper and ultrasound;

reacting the product of the previous steps, radio-iodinated benzenesulfonic acid, with phosphorus pentachloride to yield $^{125}$I-pipsyl chloride.

O-phthalaldehyde may be modified to contain radioactive iodine as a derivatizing agent for primary amines (and for amino acids, peptides and proteins) and thiols. The starting reactant is 4-amino or 4-nitrophthalic acid, and the following steps are performed:

reducing the amino-compound with lithium aluminum hydride, which, after hydrolysis, is followed by exhaustive extraction of the reaction mixture with THF yielding amino-diol;

reacting with nitrous acid and with sodium iodide (Na$^{125}$I) in the presence of powdered copper and ultrasound yielding the iodinated product which is then oxidized with pyridinium chlorochromate to give 4-$^{125}$I-iodophthalaldehyde. Alternatively, higher yield may be achieved when the modified Sandmeyer reaction is carried out with non-radioactive iodide and the product is reacted, first with hexabutylditin and tetrakis (triphenylphosphine)palladium(0), and then with sodium iodide (Na$^{125}$I) and an oxidizing agent.

Radio-iodine labeled 1,2-diphenylethylenediamine may be used a derivatizing agent for catechols, catecholamines and reducing sugars. The starting reactant is p-bromobenzaldehyde and synthesis includes the following steps:

performing a benzoin reaction in the presence of cyanide ions to form racemic p-bromobenzoin, which is oxidized with chromium oxide in pyridine to non-chiral p-bromobenzil;

reacting p-bromobenzil with copper(I) $^{125}$I-iodide in glacial acetic acid (150° C.) or with hexabutylditin and tetrakis (triphenylphosphine)palladium(0) and then with sodium iodide ($^{125}$INa) to yield radioactive p-iodobenzil;

forming dioxime with hydroxylamine and subsequent reduction to produce 1,2-di(p-$^{125}$I- iodophenyl) ethylenediamine;

performing column chromatography to separate diastereoisomeric products.

Radio-iodophenylhydrazine may be used as a derivatizing agent for aldehydes and ketones. The starting reactant is phenylhydrazine and synthesis includes the steps of:

protection of the hydrazine group;

nitration of the aromatic ring which are subsequently reduced to amine and reacted with nitrous acid and sodium iodide to give p-iodo-substituted protected phenylhydrazine;

reaction with hexabutylditin and tetrakis (triphenylphosphine) palladium(0) and then with sodium iodide (Na$^{125}$I);

deprotection producing p-$^{125}$I-iodophenylhydrazine.

Appropriate derivatives of ethylenediamine-tetraacetic acid or diethylenetriaminetetraacetic acid complexed to radioactive isotopes of lanthanides such as radioactive isotopes of europium (Eu$^{3+}$) (radio-europium chelates) may serve as radiophores for amines, alcohols or thiols.

The components of a separated mixture may either contain more than one functionality of a given type which can form stable derivatives with the radiophore or contain more than one functionality which can form derivatives with the radiophore. Adjustments to the counting/detection protocol may be necessary to adjust the quantitation for such components.

Chromatography according to the invention may be applied to a mixture containing similar compounds differing significantly in their concentration. The following steps may be performed to enable quantitation of compounds present in the mixture in very small amounts despite the presence of other similar but more abundant components in the mixture:

performing chromatography of the mixture and separating fractions using the appropriate fraction collector;

treating fractions suspected of containing compounds of interest with a relatively small excess of radiolabeled derivatizing agent;

after completion of derivatization, treating the fractions with an affinity reagent, preferably solid phase, such as in polymer beads, containing the appropriate functionality to remove the excess derivatizing agent;

separating the affinity reagent, e.g. sedimentation, filtration, or for ferromagnetic core beads, magnetically separating the beads;

quantitating the derivatized fractions with multiphoton detection.

Separation may be performed using TLC and the following steps may be performed to prevent derivatization of non-interesting but abundant components of the mixture:

separating the mixture using TLC (e.g. in a developing chamber);

making a series of windows on the TLC plate at the locations obtained by calculation or calibration;

spraying the TLC plate with the radio-labeled derivatizing agent through the windows;

removing the excess derivatizing agent from the plate either by washing the plate with an appropriate solvent or with a solution of compounds containing appropriate functionality;

quantitating the TLC plate by scanning or spatially resolving multiphoton detection.

The separation may be frozen either by stopping the solvent flow or by using non-desorbing solvents or those with weak desorbing power and submitting the column itself to detection using scanning or spatially resolving multiphoton detection.

According to the invention, 3,5-di-($^{125}$I)iodo-4-methoxy compounds may be prepared and used as derivatizing agents for various classes of analytes of interest. These compounds include 3,5-di-($^{125}$I)iodo-4-methoxybenzenesulfonyl hydrazide,3,5-di-($^{125}$I)iodo-4-methoxyphenyl isocyanate, meso-1,2-bis(3,5-di[$^{125}$I]iodo-4-methoxyphenyl) ethylenediamine, and 3,5-di-($^{125}$I)iodo-4-methoxybenzoyl chloride. The starting material is reacted with an excess of radioiodide (or bromide) with Chloramine-T or similar compound, and HPLC of the reaction material is performed to isolate the reagent.

Radio-iodinated methoxybenzenesulfonyl hydrazide may be used as a derivatizing agent for aldehydes and ketones. The starting material is 4-methoxybenzenesulfonyl hydrazide.

Radio-iodinated methoxyphenyl isocyanate may be used as a derivatizing agent for a primary amino group. The starting material is methoxyphenyl isocyanate.

Radio-iodinated meso-1,2-bis(4-methoxyphenyl) ethylenediamine may be used as a derivatizing agent for catechols and reducing sugars. The starting reactant is meso-1,2-bis(4-methoxyphenyl) ethylenediamine.

Radio-iodinated methoxybenzoyl chloride may be used as a derivatizing agent for hydroxy groups. The starting reactant is methoxybenzoyl chloride.

Radiophores for multiphoton emission enhanced chromatography according to the invention comprise a first moeity bound to a multiphoton-emitting radioisotope, and a second moiety that is reactive with a functional group of an analyte of interest. The first moiety may be bound to a plurality of multiphoton-emitting radioisotopes.

In one embodiment, the first moiety is a benzene group having an alkoxy, amino, or thiol group at position 1, or another substituent providing increased electron density, the radioisotope is a halogen at position 2 or 6, such as iodine, and the second moeity is at position 4. In another embodiment, the first moiety is a complexing agent able to form a stable complex with metal and the radioisotope is a lanthanide or heavy metal. In a third embodiment, the first moiety is a crown ether, corronand, cryptate, or cryptand.

The radiophores of the invention differ from the prior art in modifications which were not previously known or suggested. For example, the use of hydroxy substituent in the Bolton Hunter reagent is undesirable according to the invention because of its reactivity.

BRIEF DESCRIPTION OF THE FIGURES

The invention is better understood by reading the following detailed description with reference to the accompanying figures.

FIG. 8: Results of studies of pre-column derivatization of GABA neurotransmitter.

DETAILED DESCRIPTION

Figure 1:
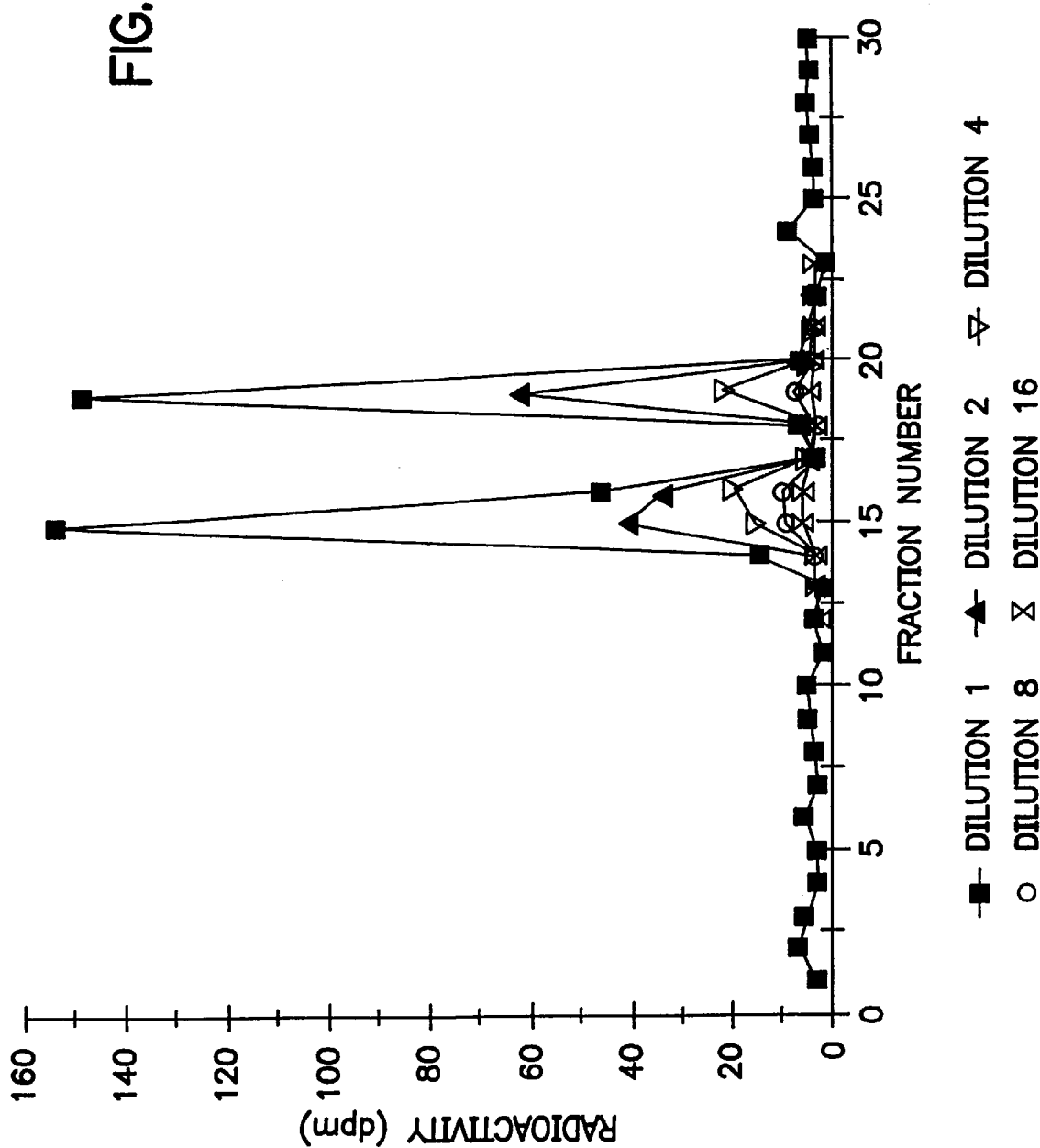
FIG. 1: HPLC/multiphoton detection measurements of binary dilutions of a mixture of estradiol and testosterone.

In describing preferred embodiments of the present invention, specific terminology is employed for the sake of clarity. However. the invention is not intended to be limited to the specific terminology so selected, and it is to be understood that each specific element includes all technical equivalents which operate in a similar manner to accomplish a similar purpose.

Multiphoton detection enhanced chromatography provides sensitivity of a few femtograms per/ml, or femtomolar concentrations. With sample sizes of 10 microliters with molecular mass of a few hundred daltons, sub-attomole sensitivity is achieved.

Multiphoton detection as described in commonly owned U.S. Pat. No. 5,532.122 has achieved sub-zeptomole/ml ($<10^{-21}$ mole/ml) sensitivity. It is understood that multiphoton detection encompasses detection as described in U.S. Pat.No. 5,532,122 and parent application 08/669,970, in coincident and/or non-coincident mode. The multiphoton detection technique applied to HPLC and TLC permits a factor of a thousand more sensitive measurements than the most popular conventional detection methods—UV absorption detection (UVD) and electrochemical detection (ECD). Techniques compatible with the use of multiphoton detection in chromatography permit significant improvement of the detection limits using Inexpensive instrumentation with sensitivity of better than $10^{-15}$ g/ml. Thus, for substances with molar masses in the few hundred dalton range, sub-attomole/ml sensitivity is achieved.

To obtain higher sensitivity, i.e. lower limits of detectability (LOD), full knowledge of the nature of the signal generation process and of background processes is required. The diverse physical, chemical and biochemical processes leading to limitations of signal to noise ratio have been elucidated and the statistical limitations to signal reproducibility have been taken into account. Previous implementations of ultra-sensitive detection systems have assumed that maximal signal detection efficiency is a necessity. Multiphoton detection is based on the finding that, contrary to common sense intuition, detection efficiency can and should be sacrificed if large gains in background rejection are achieved thereby. This novel strategy has permitted a few orders of magnitude sensitivity increase for quantitation tasks, including about a thousand-fold increase in sensitivity for chromatographic applications.

For example, multiphoton detection features very high sensitivity and high throughput for target substances labeled with electron-capture (EC) isotopes. High sensitivity is achieved through the use of state-of-the-art detector elements, complemented by very efficient rejection of all background events lacking the distinctive signature of an EC decay. The EC event signature is a coincidence of two energetic photons, typically an X-ray and a gamma-ray which originate from atomic and nuclear transitions, respectively. The radioactive background of the best multiphoton detection devices is several counts per month, as contrasted to the 10–100 counts per minute typical of commercial instruments employing single photon or electron detection. This permits detection of 0.01 pCi ($10^{-14}$ Ci) sources, or a few zeptomole ($10^{-21}$ mole) sensitivity. To increase the throughput, a spatially resolving multiphoton detection instrument may be used to permit concurrent quantitation of about 50 radiolabeled sample dots on a membrane support, each as small as a few zeptomole, multiphoton detection-Imagers are especially useful for quantitation of TLC.

The residual background with multiphoton detection may be less then one count per week (1 cpw) for EC sources. For the EC isotope $I^{125}$, this corresponds to a detectability of 600 atoms. The detectability varies inversely with the isotope half-life, so that a few atoms detectability can be approached by using shorter half-life isotopes, e.g $I^{123}(t_{1/2}=10$ h). Sequentially sampling multiphoton detectors (SS-MPD), spatially resolving multiphoton detectors (SR-MPD), scanning multiphoton detectors (SC-MPD) and multiphoton detection imagers (MPDI) may be employed according to the invention. Throughput can be increased by simultaneous quantitation of multiple samples, especially if each sample consists of species with distinguishing isotopic labels.

For samples to be analyzed through a fractionation process, it is generally desirable to minimize the input volume. In the fractionation process itself the volume of the input sample limits the resolution of output species. Two species are generally deemed "resolved" if their separation is more than their output band half widths. Thus for optimal resolution, inputs which just enable quantitative readouts by the detection system are preferable.

Any marked improvements in detection system sensitivity enables increased resolution by allowing decreased sample input, but introduces new problems in total system management. Sample species in general tend to be lost by a combination of factors. Optimizing the benefits of improved detection is achieved through a recursive process of:

quantitation of outputs and losses;

deducing causes of sample loss;

designing countermeasures;

evaluating countermeasures with respect to maintenance/improvement of resolution and sample recovery.

Multiphoton detection enhanced chromatography according to the invention achieves a desirable tradeoff between optimal resolution and maximal sample recovery.

According to the invention labeling chemistries are provided for desirable EC and PG isotopes in implementations involving many families of macromolecules. When a molecule of a target compound can be labeled with several atoms of radioisotope, detectability is considerably enhanced. With this strategy the detectability of a single macromolecule may be possible. With such high detectability, the paramount problem is implementation of complementary improvements.

The use of multiphoton detection and complementary novel derivatization methods, and system optimizations, are especially important for chromatographic fractionation methods, e.g. HPLC, TLC, GC, and CE and gel electrophoresis.

Pre- and post-fractionation derivatization techniques appropriate for multiphoton detection enhanced chromatography according to the invention are new, enabling techniques which can be applied to a wide variety of purposes. Multiphoton detection permits the ultra-sensitive detection and quantitation of isotopes from a family of electron capture (EC) radioisotopes, including $I^{123}$, $I^{124}$, $I^{125}$ and $I^{126}$. Multiphoton detection reduces the background to a level of about 0.5 counts per week (0.5 cpw), with resultant limits of quantitation down to 0.01 picoCurie activities of radio-isotope. This corresponds to about a few zeptomole level of detection for $I^{125}$ labeled macromolecules.

The virtual elimination of background increases sample throughput, especially with a spatially resolving multiphoton detection (SR-MPD) system which permits concurrent quantitation of about 50 samples with a sensitivity of almost $5 \times 10^{-21}$ mole per sample. Multiphoton detection quantitation at the few attomole level requires only a few minutes' measurement time. Due to their distinguishable gamma "signature", a plurality of EC different co-resident EC isotopes can be simultaneously and independently quantitated. An MPD system according to the invention allows simultaneous discrimination of up to 16 different radio-isotopes. An additional advantage of multiphoton detection is that it is an add-on feature to enhance quantitation for any conventional or new chromatographic equipment.

There are three main modalities for analytical use of HPLC columns. The detection is done either in-flight, or is done after the effluent is caught in a fraction collector or on an appropriate membrane or filtration substrate. When the effluent is trapped onto a filtration medium, e.g. paper filters, one-dimensional continuous distributions of effluents are formed during fractionations. It is, however, possible to create more compact two dimensional distributions, wherein the effluent is collected for a precise interval of time in one spatially restricted "dot". Successive dots may be "raster scanned" onto the membrane, creating a two-dimensional pattern. These "chromatographic dot blot" patterns are usually deposited on reasonably robust membranes, which are then used for further quantitative image processing. Appropriate chemistry can be initiated to attach multiphoton detection tags to the specific effluents and multiphoton detection-imagers may be used to quantitate the resultant pattern.

The chromatographic dot blot allows a desirable application of spatially resolving multiphoton detection detectors and multiphoton detection-imagers. Using a spatially resolving multiphoton detection device with sub-millimeter resolution blots were quantified and dot/bars patterns spatially resolved at the sub-attomole level.

Potentially, an important advantage of multiphoton detection is the possibility of using many radiolabels which can be recognized by the characteristic energy of the emitted photons. The capability of the multiphoton detection system to distinguish among emitters with different energy is "multicolor", even though the photons are much more energetic than visible light photons. Thus, co-resident effluent distributions (multicolor chromatographic dot patterns) can be quantitated.

The relative merits of on-line and off-line monitoring of the chromatographic process may be evaluated in terms of cost and throughput when both UVD and multiphoton detection are operated at the same sensitivity, even though multiphoton detection may be operated at a thousand times more sensitivity. In the case of TLC up to 20 samples can be introduced onto a single, low cost plate. Up to 15 plates can be read-out in parallel by the same spatially resolving multiphoton detector. Thus, the throughput of multiphoton detection detectors operated in off-line mode can be much faster than that of UVD detection. This comparison is valid for both multiphoton detection and UVD applied to the plate after removal from the developing chamber.

Typically, detection of products on a TLC plate is done after the TLC plate has been developed. Using TLC, one-dimensional (1-D) continuous distributions of eluent are formed during fractionations. Scanning multiphoton detection instruments are well suited for 1-D chromatograms. However, when more than one sample is spotted on one TLC plate, it is possible to create more compact two dimensional (2-D) distributions. Spatially resolving multiphoton detection and multiphoton detection imagers may be used to quantitate the resulting 2-D chromatograms. Their advantage is that the time necessary to measure all dot blots will be decreased in proportion to the number of distinguishable pixels.

HPLC columns can be operated in a mode analogous to a TLC plate, i.e. in the mode wherein the mixture of analyte is resolved within the column, but prior to exiting the column. Thus, in another implementation of HPLC/multiphoton detection, the separation is frozen within the column either by halting the solvent flow or by the use of solvents with negligible desorbing power, following which the column itself is submitted to detection using either a spatially resolving or scanning multiphoton detection.

In the case of TLC the separation step leads to a 2-D distribution of separated products which can be quantitated by multiphoton detection imagers. Either pre-fractionation or post-fractionation derivatization can be used. In some cases, however, the analyte of interest is present in low amounts whereas other analytes with similar functionality are present at a few orders of magnitude higher amounts. In this case a special implementation is advantageous, wherein the separation is performed using TLC. Herein, the separation process is initiated and stopped after a pre-calibrated time, following which the plate is sprayed with radiophore agent through a window which masks all parts of the plate except those portions at which the desired analyte is expected to be. This methodology prevents derivatization of the non-interesting but more abundant components of the mixture. The excess of derivatizing agent is removed from the plate either by washing the plate with an appropriate solvent or with compounds containing appropriate functionality.

In innovative immunochromatographic techniques according to the invention, the strong binding between antibodies and epitopes defines the dynamics of propagation of analytes in specially prepared HPLC columns or TLC plates. The use of immunological reactions is one of the implementations of post-fractionation derivatization.

Furthermore, according to the invention the dynamics of analyte migration may be defined by competitive binding. This innovative chromatographic procedure uses the radioactive (hot) equivalent of the non-radioactive (cold) component of the separated mixture when the quantitation of only one component of the mixture is of interest. The decrease of radioactivity of the known amount of hot equivalent of the compound of interest enables quantification. The known amount of the radioactive (hot) compound is placed in those fractions after chromatographic separation where the compound of interest is expected to be present. The mixture of cold and hot compound is then treated with the appropriate reagent for the functionality present in the compound bound to the solid phase (e.g. polymeric beads). The washed beads are then measured using multiphoton detection. Alternatively, the liquid phase can be quantitated.

Multiphoton detectors for chromatography should feature ultra-high sensitivity, very good linearity and dynamic range, good spatial resolution, and high throughput. Multiphoton detection systems are especially sensitive for isotopes which decay with the coincident production of two or more high energy photons, including many electron capture (EC) and positron + gamma (PG) decay channels. The PG decay culminates in the production of a nuclear gamma and two 511 keV gammas as the positron annihilates with a capturing electron. See U.S. Pat. No. 5,083,026, which is incorporated herein by reference. Multiphoton detection is the optimal detection technique for EC and PG radioisotopes, which are found among the halogens, including $I^{125}$, heavy metals and lanthanides. There are about one hundred EC isotopes suitable as labels. The decay of EC isotopes leads to the emission of two high energy photons, typically one X-ray and one gamma-ray. In pre-multiphoton detection detectors, $I^{125}$ labeled molecules are quantitated with background of 20–40 cpm, with the consequence that single assays usually begin with about ten nCi of isotopes. Multiphoton detection marks a new milestone in sensitivity, permitting detection of a few hundred atoms and zeptomole amounts of material is possible. Even for applications requiring large throughput, multiphoton detection techniques require less than 1 pCi of isotope, i.e. about a thousand times less activity than conventional methods.

Multiphoton detection permits reliable measurement with very high dynamic range. Measurements of serial dilutions show excellent linearity (within 1%) over nine orders of magnitude of label concentration down to 0.1 zeptomole level. For a few pCi source, an excellent signal to background ratio (S/B >10) is obtained within a few minutes, and one can reliably quantitate 0.01 pCi $I^{125}$ sources in about one hour. The reproducibility of measurement for a few pCi source is within 1%. According to the invention, the statistical uncertainty in the case of measurements of very small amounts of radiolabels, down to sub-pCi, is quite small. For example, with multiphoton detection, a less than one minute measurement time per sample permits reliably establishing the presence of the labeled analyte; a less than 1% rate of "false negative" and "false positive" results for a few attomole concentrations of target molecules labeled with atoms of $I^{125}$. When $I^{123}$ is used, this time can be decreased to a few seconds.

Spatially resolving multiphoton detection and a multiphoton detection imager both permit considerable improvements in throughput of multiphoton detection enhanced chromatography. More specifically, spatially resolving multiphoton detector permits the fast and sensitive read-out of 2D chromatographic blots. Excellent sensitivity is achieved because with a background of 1 count per day per sample, one can detect activities as low as 0.01 pCi per sample. The concurrent detection of 50 samples, each with less than $10^{-20}$ mole of biological material has been achieved. With such parallel read-out, low count rates in individual samples do not limit overall throughput.

Multiphoton detection in scanning mode permits sub-millimeter resolution which is useful in quantitation of 1-D continuous distributions, e.g. obtained as an output of fractionation processes such as HPLC or electrophoresis. Similar resolution has been demonstrated for 2-D continuous distributions of biologicals using the multiphoton detection-Imager.

A multiphoton detection imager is an innovative device wherein a spatially resolving multiphoton detector is coupled with the appropriate movement of a scanning table compatible with the use of 2 D chromatograms. Coordination of the scanning table with the signal acquisition software permits "seamless" reconstruction of activities when using a plurality of apertures, each placed in front of a pre-defined region of interest (ROI) of the spatially resolving multiphoton detector. Importantly, even if the detection efficiency varies considerably over the surface of the spatially resolving multiphoton detector, the hardware/software combination permits reproducible quantitation of arbitrary 2 D distributions of EC isotopes.

In chromatographic applications, it would present a problem if EC radioactivity was present in solvents and components of the chromatographic column matrix. Fortunately no EC radioactive background could be detected in many fluids, such as water, ethyl alcohol, benzene, and trichloroethylene; in selected biochemical compounds; in columns, microcapillaries, Eppendorf tubes and diverse plasticware. The natural contamination of selected physiological liquids with EC isotopes is at least four orders of magnitude lower than of a single beta or gamma emitters, e.g. $K^{40}$ or $C^{14}$. Thus, when an multiphoton detection device is used, the background radioactive background is negligible.

In Examples 1 and 2, multiphoton detection was used to enhance the sensitivity of HPLC for neurostimulants and sex steroid hormones, respectively. In Example 3, the separation of sex steroid hormones by TLC was studied. Example 4 involves pre-fractionation derivatization of a plurality of substances of interest, including amines.

EXAMPLE 1

An assay mix of $^{125}I$ SCH-23982 (concentration between $5\times10^{-17}$ and $3\times10^{-15}$ moles; activity between 6 cpm and 160 cpm), an antagonist of dopamine, in TRIS buffer was mixed with cold I SCH-23982 (concentration between 0 and $3\times10^{-13}$ moles) for analysis by reverse phase HPLC. The HPLC column was a SUPELCO Supelcosil C-8, 15 cm ×4.6 mm, 5 μm particle, preceded by a guard column of the same packing. The gradient used was 5 minutes at 100% water followed by a gradient ramp of 5% ethanol per minute to a final solvent mix of 75% ethanol and 25% water for 5 min before returning to 100% water for 15 minutes before the end of the run. The flow rate was 0.5 ml/min and the pressure was stable at 650 psi. Fractions were collected every minute for 24 min, then every 1.8 min until the end of the run. A photodiode array detector set between 200 and 400 nm was used (I SCH-23982 has a $\lambda_{max}$ of about 210 nm) during the run to monitor elution of cold substrate.

The radiolabeled molecules do not decompose during chromatography and the limits of detection were several orders of magnitude better than when the same column eluent was submitted to a UV detector. Reproducibility of three measurements was better than 5% at the pg/ml level. For the same sample, UVD was not able to detect any chemicals in fractions even though the amount of cold (iodinated with non-radioactive isotope) anti-dopamine was a thousand times higher than the amount of analog labeled with $I^{125}$, which was easily quantitated with multiphoton detection. Moreover, the integrated activity in the peak corresponding to the radiolabeled product changed linearly with sample volume over three orders of magnitude, ie. from a few fg/ml to at least a few pg/ml.

EXAMPLE 2

In the second set of experiments, sex steroids with $^{125}I$ labeled histidine moiety attached were studied, namely testosterone-3-(O-carboxymethyl)oximino-(2-[$^{125}I$] iodohistamine) and oestradiol-6-(O-carboxymethyl) oximino-(2-[$^{125}I$] iodohistamine). The separation of iodinated steroid hormones (Amersham) were performed using a Perkin-Elmer instrument with Binary LC Pump 250, PE Pre Column Scavenger and C18 Cartridge Column (3.3 cm length with particles of 3 microns diameter). The flow was kept constant at 1 ml/min and 1 ml fractions were collected for 35 minutes. The columns were kept at room temperature. All the fractions were measured by an multiphoton detection device for 1 minute, and a few fractions containing some radioactive material were remeasured for a longer time. The solvent system consisted of acetonitrile and water (both from Fisher). At first, the column was washed with a mixture containing 10% acetonitrile. After sample injection the linear gradient was such that the final concentration (10% water) was reached after 30 minutes.

Since non-radioactive analogues were not available, studies with higher concentrations of cold (non-labeled) compounds and standard detectors were not performed. To measure the sensitivity of HPLC/multiphoton detection, the individual compounds were dissolved in a methanol/water (9:1) mixture and diluted to about 100 fg/ml. A sample of 10 microliters of this solution was injected to the chromatographic system. It corresponded to a total sample radioactivity of a few hundred dpm, ie. about 100 pCi. Then, the solutions of individual steroids were submitted to HPLC and the fractions were collected and measured using the multiphoton detection device. In the case of both labeled steroids the column eluent contained only one peak and its intensity was very consistent with the original sample radioactivity. After determining the conditions for which the retention times were different for both compounds, testosterone and estradiol derivatives were mixed and diluted to less than 100 fg/ml. This mixture was submitted to chromatographic separation under the same conditions as in previous experiments, collected in 1 ml fractions and measured using the multiphoton detection device.

Figure 2:
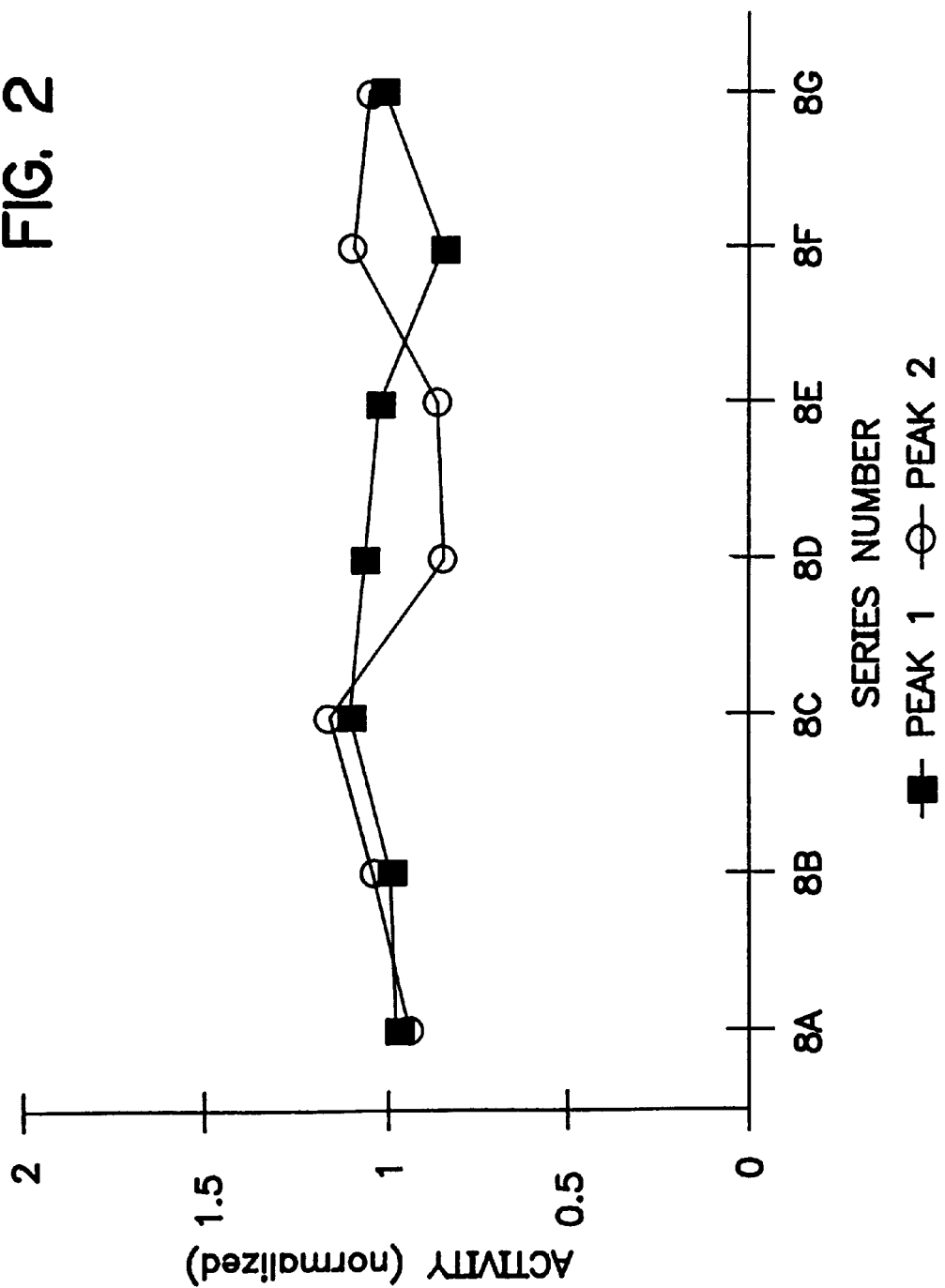
FIG. 2: Reproducibility of HPLC/multiphoton detection measurements of about 20 attomole/sample of the mixture of estradiol and testosterone; the integrated count rate in each of the two peaks is plotted. The data are normalized to the average of the integrated activity in each peak.
Figure 3:
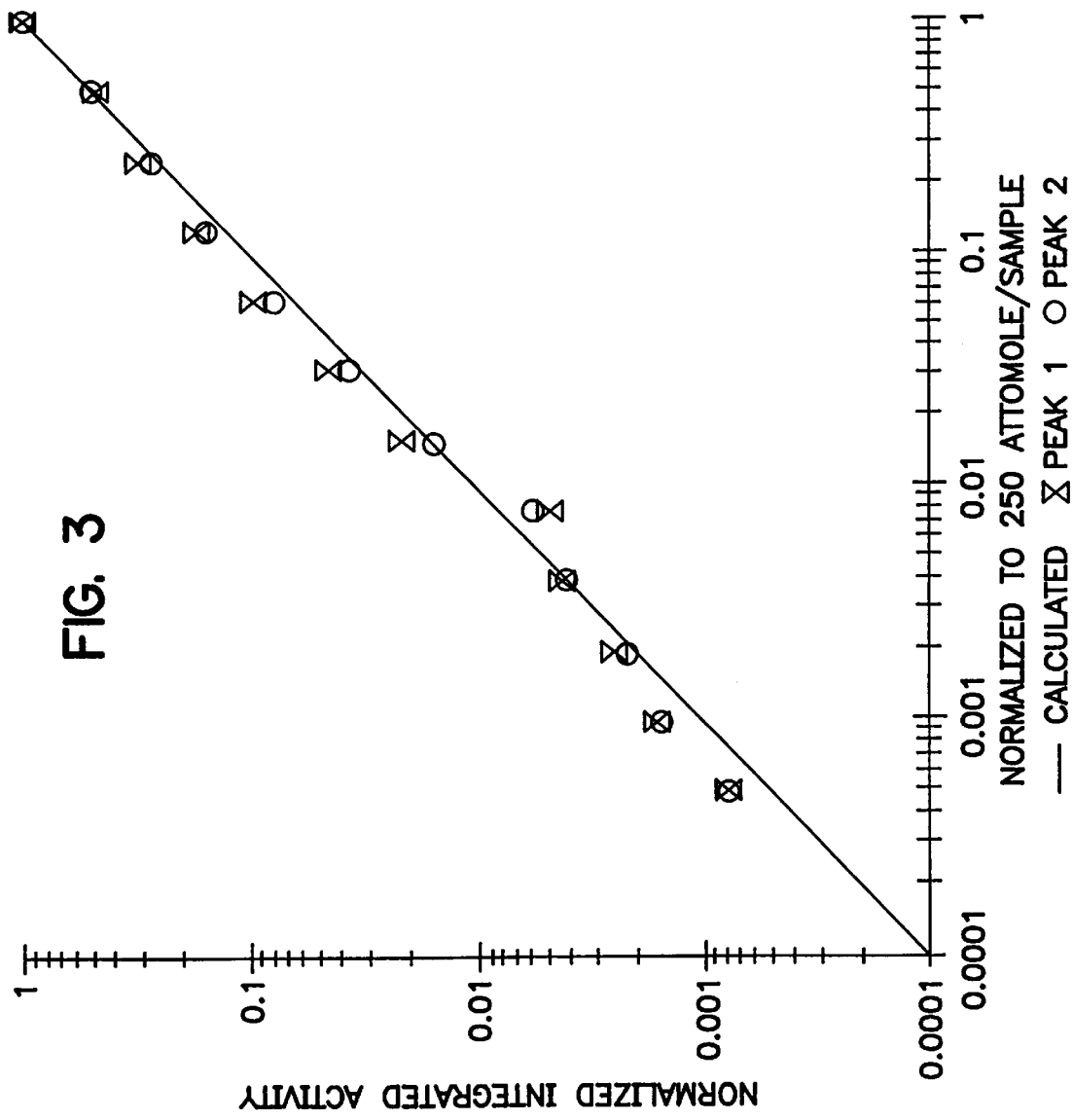
FIG. 3: Linearity of HPLC/multiphoton detection measurements of a mixture of steroidal hormones; the results for binary dilutions down to factor 1:2048 are shown. The lowest point corresponds to 0.12 attomole/sample.

Even for this very diluted mixture of steroids one can see very well resolved peaks, each showing a high ratio of signal to noise (S/B). During these preliminary studies four more mixtures were submitted to the separation and measurement described above. These mixtures were the result of serial binary dilutions of the first mixture. FIG. 1 shows the results of the measurements of the collected fractions for HPLC separations of the original mixture and the 2, 4, 8, and 16-fold dilutions. This last dilution corresponds to a concentration of about $10^{-17}$ mole/ml. Even for this ultralow concentration the signal can be distinguished easily from the background (S/B >120). FIG. 2 shows the excellent reproducibility for seven different HPLC separations of the factor 8 dilution mixture; even at the 20 attomole/sample level excellent reproducibility is observed. Finally, FIG. 3 shows the results of HPLC separation of binary dilutions of a testosterone and estradiol mixture; note the good linearity for dilutions down to 0.1 attomole/sample.

EXAMPLE 3

In this experiment the same mixture as used in experiment 2 was submitted to TLC separation; using reverse phase (5 cm ×10 cm) TLC glass plates with silica (Merck, RP-8 $F_{254}$). The solvent system used was acetonitrile and water (2:1), and the separation was performed at room temperature.

Figure 4:
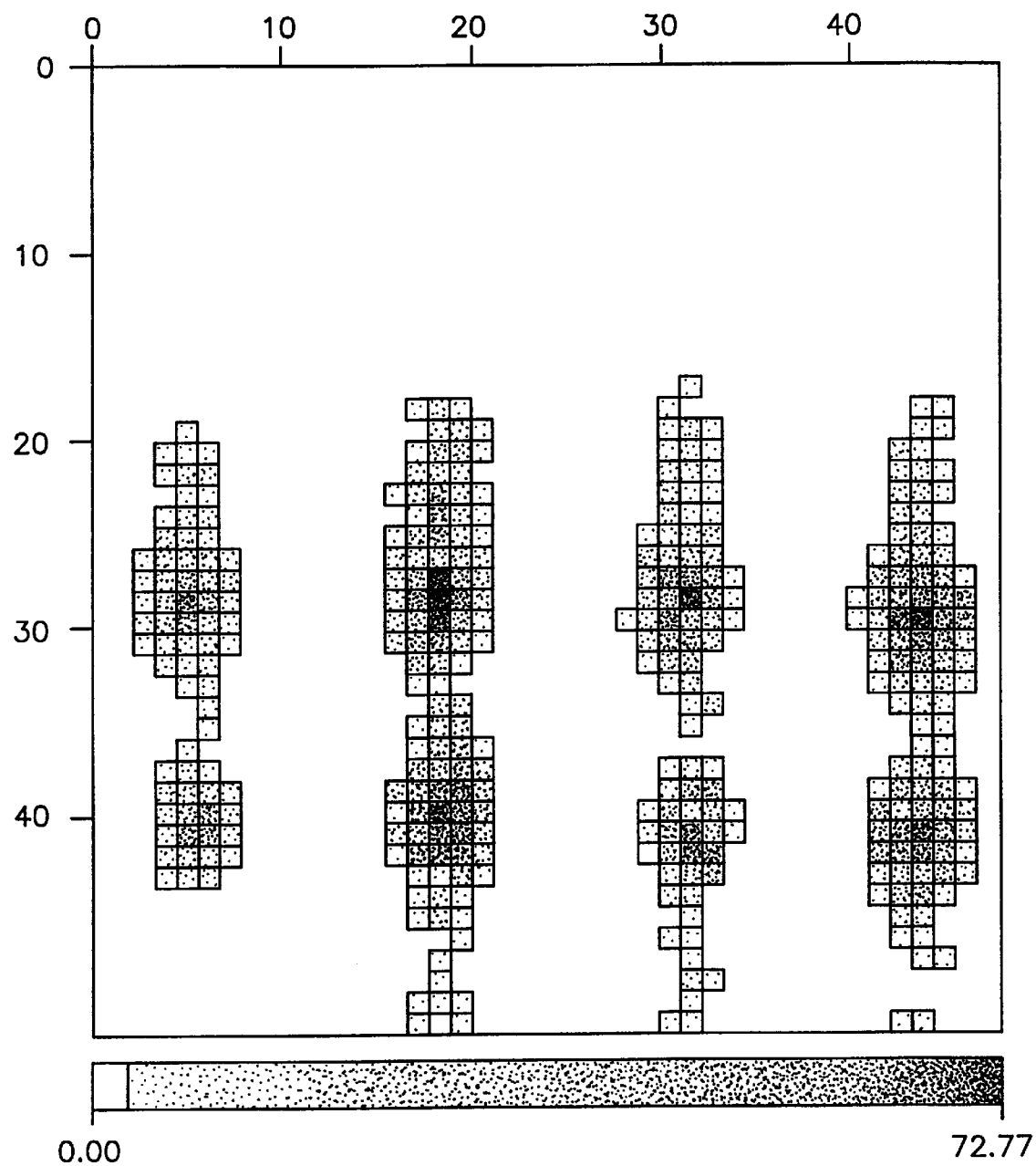
FIG. 4: Measurements of a mixture of steroids using TLC/multiphoton detection; the images are for four 10 microliter samples, each at a concentration of 0.12 pg/ml. Distances are given in millimeters; the count rate is shown as counts per minute per 2 mm$^2$ pixel according to the key.
Figure 5:
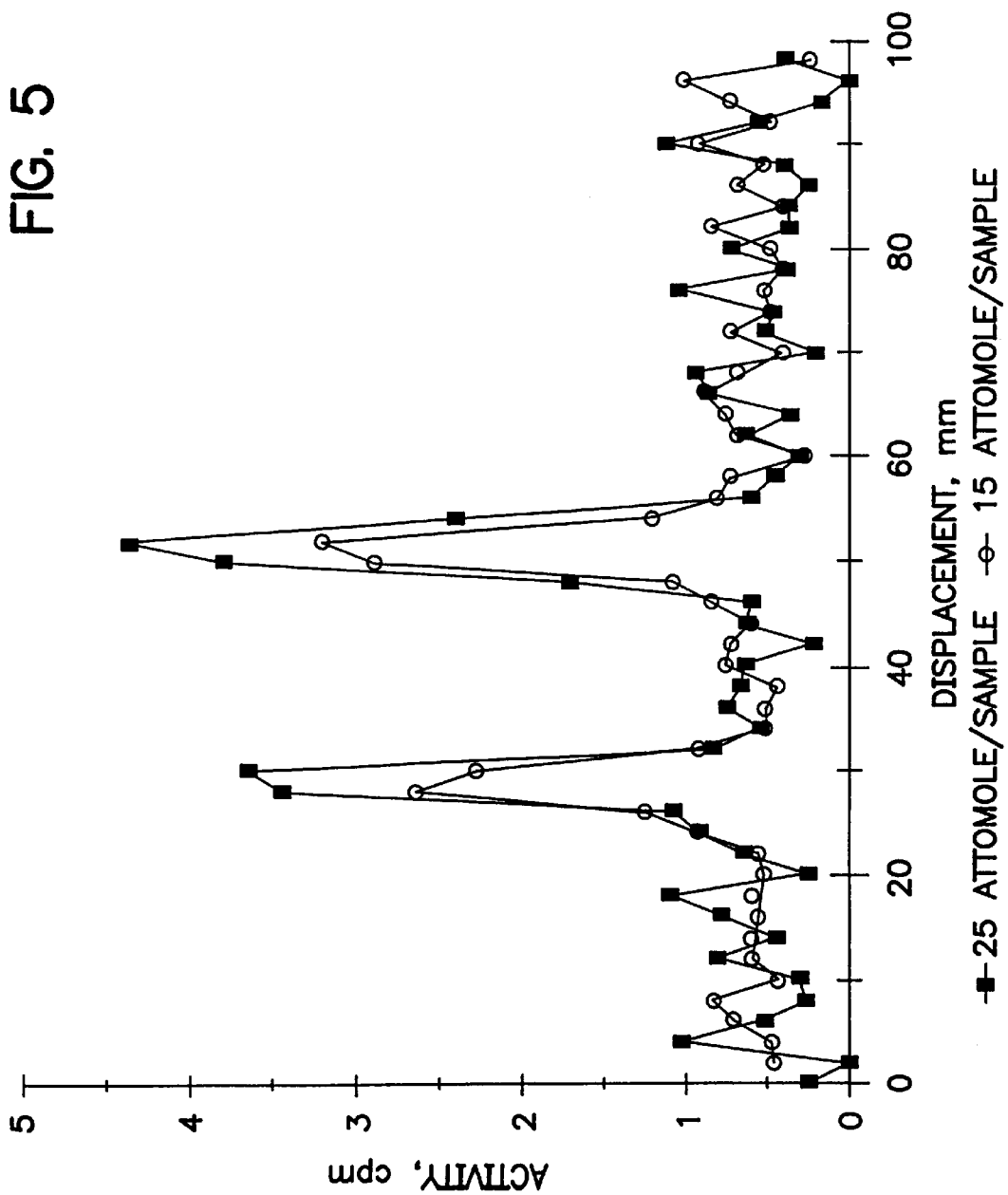
FIG. 5: TLC separation of ultra-low concentrations of a steroid mixture (estradiol and testosterone); the plotted curves are the scans along each lane for samples with concentration of 25 attomole/sample and 15 attomole/sample, respectively.
Figure 6:
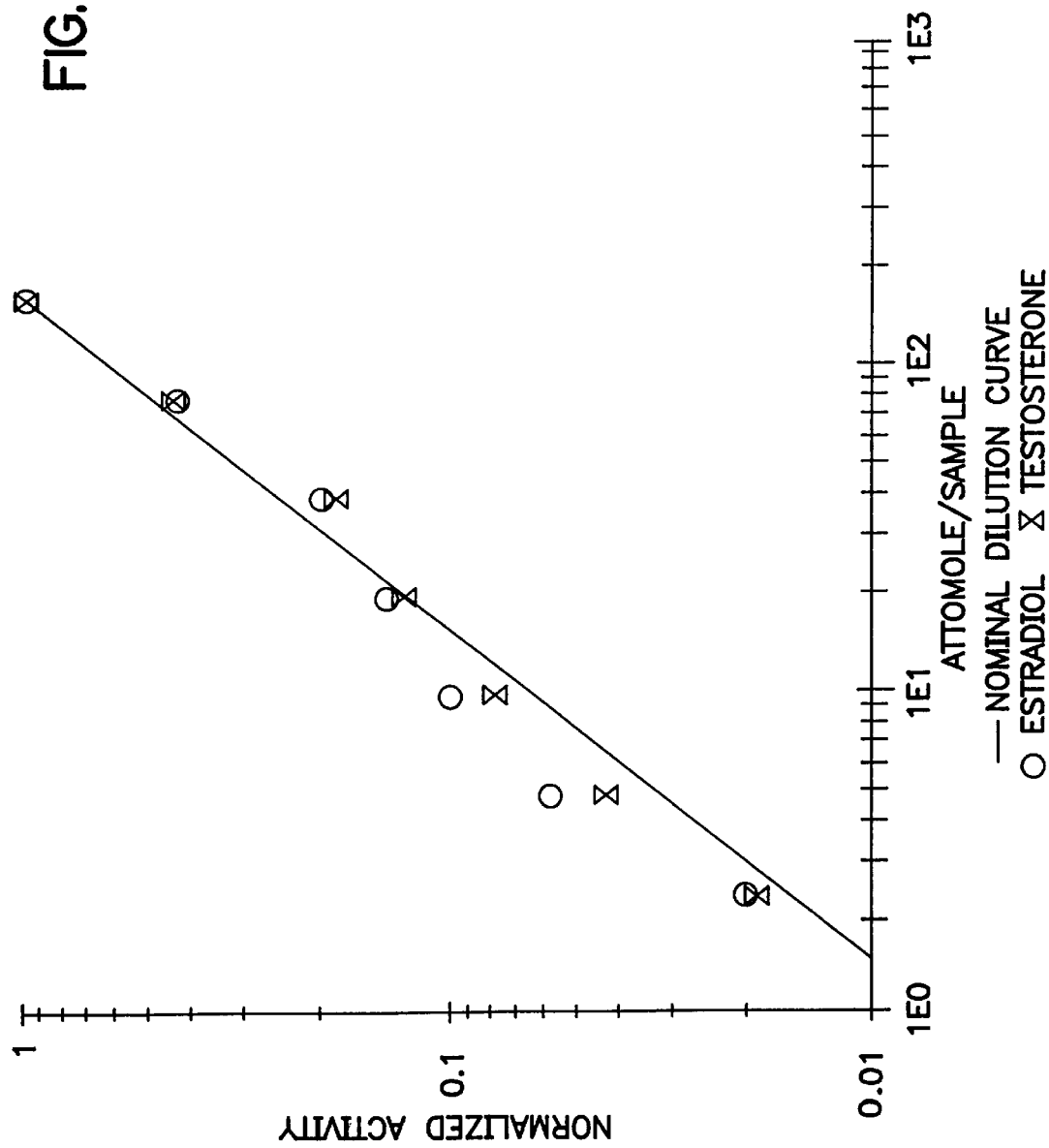
FIG. 6: Linearity of TLC/multiphoton detection measurements of a mixture of steroidal hormones. The results are for dilutions down to a factor of 1:128; the lowest point corresponds to 2 attomole/sample.
Figure 7:
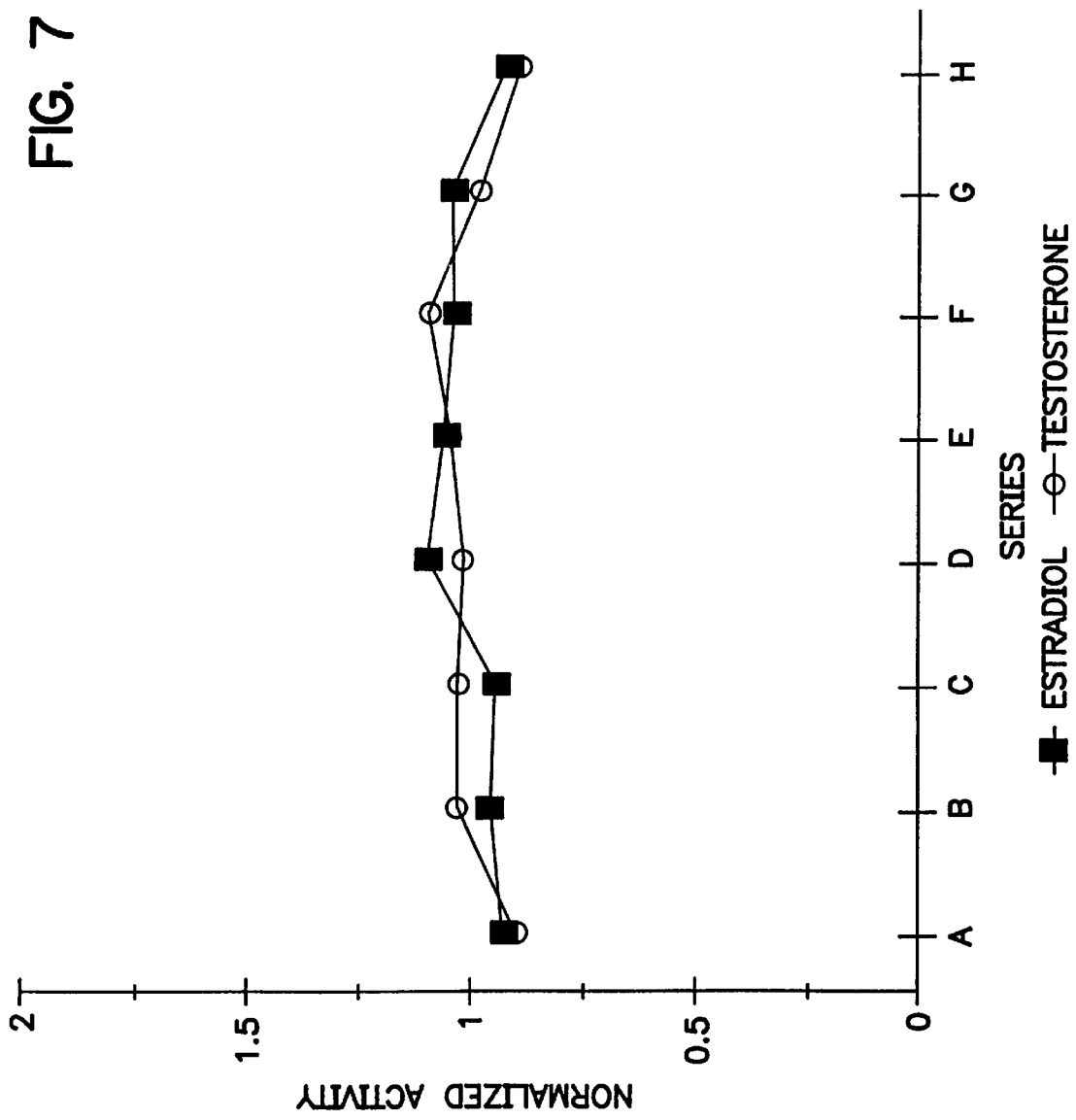
FIG. 7: Reproducibility of TLC/multiphoton detection measurements of a 40 attomole/sample of a mixture of estradiol and testosterone. The graph shows the integrated activity in each peak, normalized to the average of all eight measurements.

To measure the sensitivity of TLC/multiphoton detection, the mixture of two steroids was dissolved in methanol/water (9:1). Four ten microliter samples of this solution were placed on a silica plate and inserted into the TLC tank. After development, the TLC plates were dried and measured with a scanning spatially resolving multiphoton detector having 2mm pixel resolution. This resolved all peaks with excellent signal-to-noise ratio (see FIG. 4). FIG. 5 shows the scan along two lanes of a TLC plate used for separation of a testosterone and estradiol mixture at very low concentrations (25 and 15 attomole/sample). Note again the excellent signal to noise ratio of these measurements, even at very low instrumental count rates. Binary dilutions of the above mixture of steroids were studied. FIG. 6 shows the results— note the excellent linearity down to 2 attomole/sample. All of these ultralow concentrations were easily detectable. The results also documented the excellent reproducibility. FIG. 7 shows eight measurements at 40 attomole/sample of the steroids mixture. Similar reproducibility has been observed for both larger (100 attomole/sample) and lower concentrations (down to 10 attomole/sample). Remarkably, the reproducibility of TLC/multiphoton detection measurements can be somewhat better than the HPLC/multiphoton detection measurements (compare FIGS. 2 and 7).

EXAMPLE 4

Figure 8A:
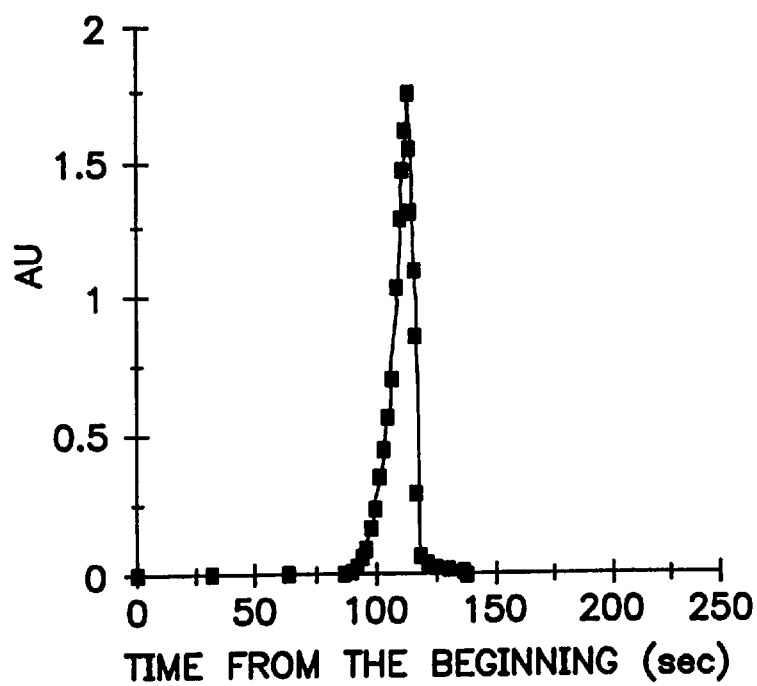
FIG. 8a presents results for UVD detection of GABA derivatized with cold pipsyl chloride.
Figure 8B:
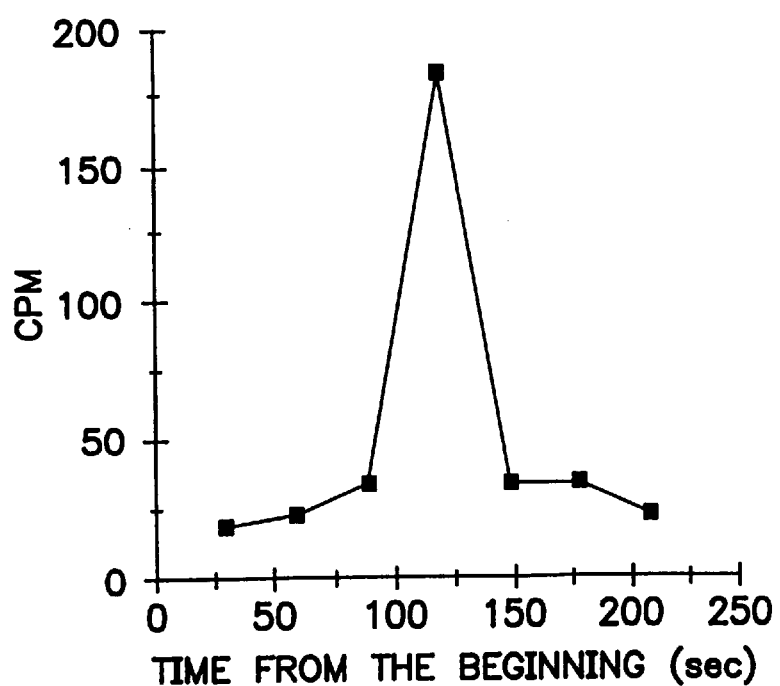
FIG. 8b presents multiphoton detection measurements of GABA derivatized with "hot" (radioiodinated) pipsyl chloride. The amount of "cold" sample was about one million times higher than that of "hot" sample. Taking into account the observed signal to background ratios, multiphoton detection is about a thousand-fold more sensitive.

In this experiment derivatization with a radiophore (derivatizing agent introducing radioactive properties to the mixture components) was performed followed by HPLC separation and multiphoton detection detection. The radioactive derivatizing agent (pipsyl chloride) was synthesized from p-aminobenzenesulfonic acid via diazonium salt formation and subsequent reaction with sodium ($^{125}$I) iodide. Next, the reaction mixture was extracted with benzene, dried and submitted to reaction with thionyl chloride. The product was reacted in the presence of triethylamine with GABA (4-aminobutanoic acid) (small excess of an acid chloride) in benzene. The reaction mixture aliquots (10 and 2 microliters) were injected to the HPLC system under conditions determined for GABA derivatized with cold (non-radioactive) pipsyl chloride (isocratic system, room temperature, acetonitrile: water=58:42). Additional experiments showed that no reaction of the pipsyl chloride with water took place during the time of separation. Subsequent quantitation using multiphoton detection confirmed the validity of the derivatization procedure. The presence of GABA-$^{125}$I-pipsic amide was detected at the few tens of attomole/sample level. At this level, S/B >10 has been observed (see FIG. 8b).

EXAMPLE 5

Figure 9:
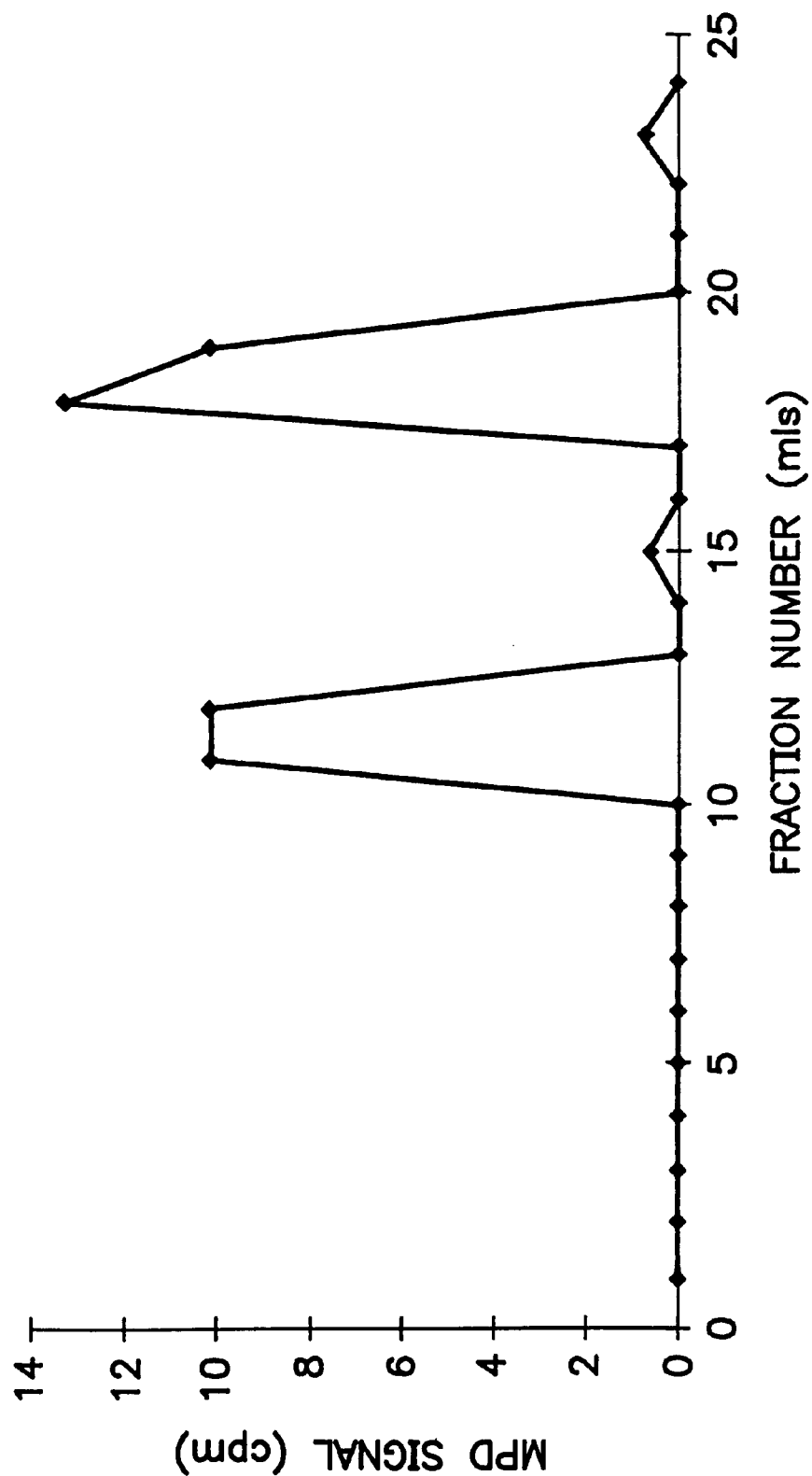
FIG. 9: HPLC/multiphoton detection using precolumn derivatization for neurotransmitters using Bolton-Hunter reagent. The two peaks represent about 50 attomole/sample each of glycine and histamine.
Figure 10:
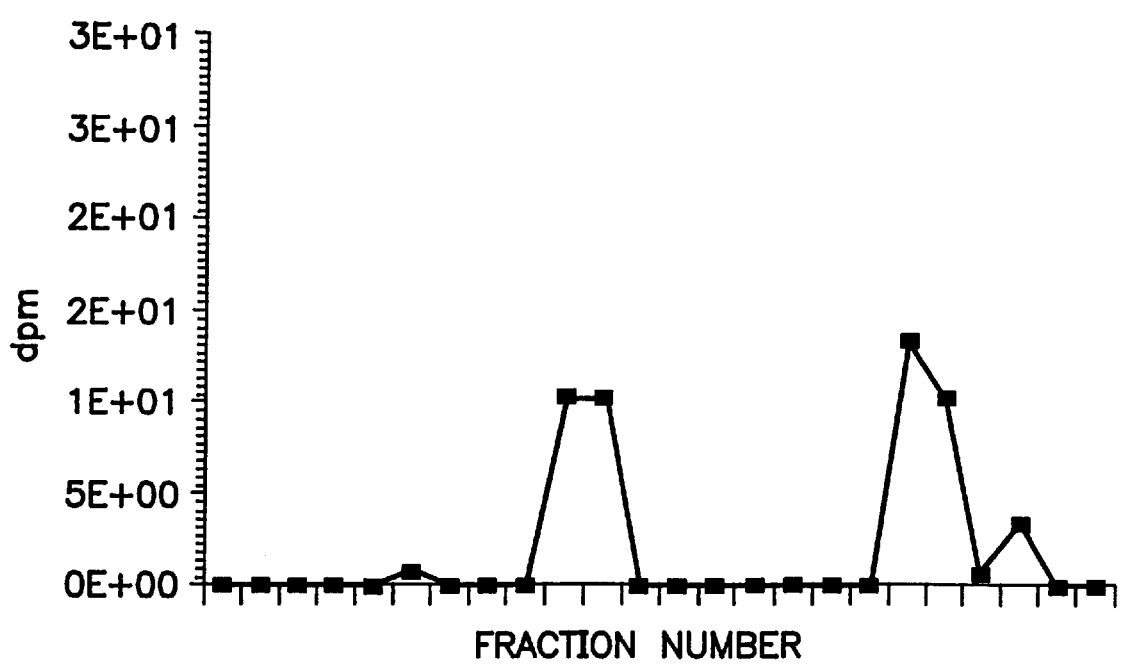
FIG. 10: HPLC/multiphoton detection of a mixture of neurotransmitters (dopamine and glycine) at the 10 attomole/sample level. The neurotransmitters were prefractionation derivatized with radioiodopipsylchloride.

In another series of experiments a mixture of neurotransmitters consisting of glycine and histamine were derivatized with diiodinated Bolton-Hunter reagent. The compounds dissolved in water were derivatized, separated by reversed phase HPLC, and quantitated by multiphoton detection at a level below 50 attomole/sample for each amine (see FIG. 9). These experiments show the feasibility of derivatization with radiophores for multiphoton detection, without attempting to achieve the limits of detection of the method. For a mixture of dopamine and glycine derivatized with pipsyl chloride, the limit of detection is apparently below 10 attomole (see FIG. 10).

Applications of Multiphoton Detection Enhanced Chromatography

Biomedical Applications

Chromatographic methods can detect and measure many molecules present in physiological fluids such as blood, urine and saliva. A patient profile comprised of multiple assays is extremely informative for the physician, but using current techniques, is often prohibitively expensive. Recently, there have been numerous attempts to introduce multianalyte testing to medical practice, but in most cases they are either not sensitive enough or are too expensive. Using multiphoton detection enhanced chromatography many concurrent assays can be performed for many analytes from a common volume/format. The physician can thus have a relatively low cost "profile" of multiple potentially relevant physiological parameters, as contrasted to a few individually expensive assay points.

Due to its traditional importance in disease detection and therapy monitoring, in vitro diagnostics is an important application for multiphoton detection enhanced chromatography. Better understanding of different biological mechanisms calls for the study of constituent materials which are present in far lower concentrations.

Multiphoton detection enhanced chromatography may be useful for in vivo studies of the uptake and metabolism of organic compounds labeled with multiphoton emitting radioactive atoms. For example HPLC/multiphoton detection and TLC/multiphoton detection can be used for in vivo pharmacokinetics studies, wherein the mixture of analytes is injected or ingested by a patient either pre radiolabeled or when it contains a type of functionality which can form stable derivatives with the radiophore.

Neurotransmitters

There is a need for more sensitive and more patient friendly methods of detection and quantitation of sub picomole amounts of amines, amino acids, small peptides, and other biologically active molecules together with their precursors and metabolites. Detection and quantitation of sub-picomole amounts of neurotransmitters and their metabolites is an important factor limiting biological studies of the functions of the central nervous system (CNS). The levels of some of these neurotransmitters decrease rapidly during diseases. The use of HPLC/multiphoton detection and TLC/multiphoton detection permits higher sensitivity and more reliable quantitation. An additional potential advantage is the possibility of measuring neurotransmitters not only in cerebrospinal fluid, but also in brain tissue or other physiological fluids.

Most neurotransmitters (NT) are primary amines. Some of them contain additionally acid or phenolic (usually catechol) functionality. The common neurotransmitters are acetylcholine; monoamines such as dopamine, epinephrine, norepinephrine, serotonin, histamine and tryptamine; peptides such as β-endorphin or methionine enkephalin; and amino acids such as glutamate, aspartate, γ-amino butyric acid [GABA], glycine.

Also of interest are the amino acid precursors of these neuro-compounds, which belong to amines such as tyrosine, tryptophan and histidine and some endogenous catechols such as dihydroxyphenylglycol, dihydroxyphenylalanine, dihydroxyphenylacetic acid.

The levels of neurotransmitters in the brain or in spinal fluid are rather high, i.e. their detection is straightforward. Alas, this leads to the need for invasive protocols and is not patient friendly. Measurement of the level of neurotransmitters in plasma and urine are of tremendous importance. However, due to the blood/brain barrier, the levels of some neurotransmitters and/or opiates in blood is many orders of magnitude lower and reliable detection is difficult. HPLC/multiphoton detection and TLC/multiphoton detection improves the existing limits of detection of brain stimulants and similar compounds at least 100-fold.

TLC and HPLC are more reliable than immunoassays when the presence of metabolites provide artifactual receptors to antibodies. Since the group of neurostimulants consists of many compounds and their metabolites are also present, it is not surprising the most often used analytical technique is HPLC. The use of chromatography is facilitated by the fact that most of the neurostimulants are small molecules. Unfortunately, existing detection methods used in chromatography are not sensitive enough for numerous diagnostic and research measurements. In the case of neurotransmitter analysis quantitative accuracy is of particular importance. For example, recent results of studies with laboratory animals and with humans have indicated that simultaneous measurements of plasma levels of dihydroyphenylacetic acid with levels of other catechols provide information about related but distinct aspects of symphathoneural function. C. Holmes, et al., J. Chromatogr. B, 653. 131, 1994. Precise knowledge of different neurotransmitter levels in body fluids such as plasma or urine is of dramatic importance to research and diagnosis.

The detection and quantitation of sub pico-mole amounts of neurotransmitters/opiates and their metabolites is an important factor limiting biological studies of CNS processes, including diseases of the elderly, e.g. Alzheimer's disease. Applications of multiphoton detection enhanced chromatography for quantitation of levels of neurotransmitters is important both on tissue and cellular levels.

Steroidal Hormones

There is a great need for refinements in techniques for the measurement of hormones such as estrogen, progesterone and other markers of ovarian function leading to enhanced sensitivity and greater economy in the cost per test. Multiphoton detection enhanced chromatography permits measurement of these hormones at the attomole level.

Immunoassays and high performance liquid chromatography (HPLC) are used as laboratory techniques for the detection of steroids. The use of TLC is a more rapid and cost effective method. The factor which up to now has limited applications of TLC for hormone analyses has been the lack of adequate sensitivity. With multiphoton detection read-out, TLC can now provide sufficient sensitivity in an inexpensive, easy to use procedure appropriate for high throughput routine screening using non-invasively obtained samples (urine and/or saliva). Because of its excellent sensitivity, linearity and dynamic range, TLC/multiphoton detection can accurately measure both the primary hormones and their metabolites, which may be present at orders of magnitude lower concentration.

For steroidal hormones the methods of the invention achieve sub-femtomole/ml sensitivity and excellent linearity. With typical samples according to a recent review of biomedical chromatography, Y. Ohkura, M. Kai, H. Nohta, J. Chromatography,B659, 85, (1994), previous methods give a few tens of femtomole/ml limits of detection for typical sex steroids. For example, in a recent paper, J. Fiet et al., Clin. Chem. 40/12, 2296–2305 (1994) studying the level of ten anabolic steroids by HPLC, the limits of detection quoted are 34 ng/ml, 70 ng/ml and 105 ng/ml for progesterone, testosterone propionate and testosterone enenthate, respectively. In another paper, S. Torres Cartas et al., Analytica Chemica Acta 302, 163–172 (1995) the levels of eight steroids were studied using coordinated radioimmunoassays (with a HPLC pre-purification step). Limits of detection of 10 fmole/sample and 36 fmole/sample are quoted for testosterone and 17-alpha-hydroxy-progesterone, respectively. Even using the most expensive analytical modality, GC/MS, the detection limit is not better than 3.5 fmole/sample. C. Legrand et al., J. Chromatography B663, 187–192 (1995). Furthermore, in this case the region of linearity is somewhat restricted to 1.7–71.5 pmole/ml.

HPLC/multiphoton detection and TLC/multiphoton detection according to the invention achieved a sensitivity of 0.1 attomole/sample and a few attomole/sample, respectively. Thus, the use of TLC/multiphoton detection permits a thousand-fold increase of sensitivity. Furthermore, it permits a larger linearity range and is much less expensive than currently used modalities for steroid quantitation. Using the prior-art techniques, detection and quantitation of sex hormones and their metabolites is difficult already at the picomole level. It is an important factor limiting the biological studies of older women. The levels of some of these hormones decrease rapidly during menopause. For example, the use of HPLC/multiphoton detection and TLC/multiphoton detection permits higher sensitivity and more reliable quantitation. An additional potential advantage of the superior sensitivity is the possibility of testing for sex hormones not only in blood, but also in other physiological fluids, e.g. urine and saliva, wherein these hormones are much less abundant.

The relatively high level of 16-$\alpha$-hydroxyestrone is indicative of high breast cancer risk. W. H. Church, et al., Advances in Chromatography, V. 128, Marcel Dekker, New York, p. 165, 1989. The high level of 2-hydroxyestrone is indicative of risk of osteoporosis. Therefore, the knowledge of the ratio of some estrogen. i.e. 17-$\beta$-estradiol, metabolites within the body is of tremendous importance. Moreover, steroid-related drugs are involved in social and ethical issues that include birth control, abortion, diet, body-building, drug abuse and drug testing.

Chromatography has been used extensively for determination of such steroids as cortisol. However, only recently, a limit of detection of tens of femtomoles for cortisol in human plasma has been achieved. H. Tabei et al., Anal. Chem. 66, 3500, 1994. When the determination of many different steroids is of concern, chromatography becomes the only methodology which can measure simultaneously low levels of various steroidal compounds.

A typical example is the detection of anabolic steroids. The current sensitivity of chromatographic methods of anabolic steroid detection in urine (few pg/mL) seems to be insufficient for applications by the athletic community. M. E. Bovingdon, R. A. Webster,J Chromatogr. B 659, 157, 1994. Another typical example is plasma or urine analysis of cortisol and its metabolites. The urinary steroid pattern was used for the diagnosis of different enzyme deficiencies such as CAH (congenital adrenal hyperplasia) in adrenal cortisol production. C. P. Martucci et al., Pharmacol. Ther. 57 (2–3), 237, 1993. For example, the same authors show that relatively high levels of dehydroepiandrosterone, which is known to be indicative of adrenal carcinoma, enabled successful diagnosis.

Practically all steroids can be pre/post column derivatized by conjugation with an appropriate agent.

Polypeptides, Including Angiotensins

With multiphoton detection enhanced chromatography, higher sensitivity and lower cost per test is expected. Better quantitation of the level of some peptides and their metabolites may lead to better understanding of the cause and effects of heart disease. Detection and quantitation of sub-picomole amounts of amino acids, and poly and oligopeptides are of particular biological importance. F. F. Hsu et al., Analyt. Biochem., 216, 401, 1994; R. Yost et al., Biol. Mass. Spectrom., 23, 131, 1994. The levels of some of these small peptides is often known only partially due to their low physiological concentrations.

Angiotensins are important oligopeptides with strong physiological effects. Octapeptide Angiotensin II is the most potent compound in this group and is involved in the control of blood tension. Currently, radio-immunoassays are used for detection but there are problems with cross-reactivity with other endogenous oligopeptides. This problem is especially important in the prediction of risk for heart attack and management of people with high blood pressure. The use of multiphoton detection enhanced chromatography permits higher sensitivity and more reliable quantitation. An additional potential advantage of the superior sensitivity is the possibility of testing angiotensins I and II not only in blood, but also in other physiological fluids, e.g. urine and saliva, wherein these oligopeptides are much less abundant.

Measurement of physiological concentrations of cholesterol is one of the most often performed diagnostic tests. Alas, cholesterol level alone is not sufficient to predict the risk of a heart attack. If reliable and low cost, the measurements of the levels of a plurality of small peptides involved in blood pressure regulation may become one of the most often performed analyses, complementary to the measurement of the level of cholesterol. A particularly important group of small peptides are those connected with the renin-angiotensin-aldosterone system, and the study of their levels can be performed in blood, but also in urine and saliva. Aldosterone release stimulates cell growth in damaged blood vessels and is a potent vasoconstrictor. Angiotensin II is physiologically active in the low picomolar range.

An immunoassay for Ang II is available (Nichols Institute Diagnostics) with a limit of detection (LOD) of about 4 pg/ml. Gas and liquid chromatography have been used extensively for determination of many amino acids and oligopeptides. There are limitations due to the insufficient sensitivity of existing detection methods, especially in the case of studies of angiotensin metabolism. With a derivatizing agent for amino acids according to the invention, one can use TLC/multiphoton detection and HPLC/multiphoton detection to study angiotensins and their metabolites. Angiotensins can be derivatized with radiolabeled iodophthalaldehyde and pipsyl chloride.

Since most steroids of interest carry the hydroxyl functionality, derivatization using the acid chloride can be used to incorporate the radio-label. Additionally, several steroids contain the carbonyl group which can be derivatized with a radioiodinated analog of p-methoxybenzenesulfonyl hydrazide or phenylhydrazine.

When determination of many different peptides is of concern, chromatography becomes the preferred methodology since it can measure simultaneously and reliably low levels of various structurally similar peptides, including angiotensins. Current sensitivity of chromatographic methods for small peptide detection in urine (few pg/mL) seems to be insufficient for applications in heart disease management. A typical example are prior-art limitations on studies of the renin-angiotensin-aldosterone system.

The detection and quantitation of sub picomole amounts of small peptides and their metabolites is an important factor limiting biological studies of the process of blood tension regulation. This problem is especially important in assessment of the risk of heart attack and in post heart attack patient management.

Other

The extremely high sensitivity of multiphoton detection enhanced chromatography for some metabolic products suggests its use in the detection of cancer, e.g. breast cancer. Furthermore, multiphoton detection-assays may be used in pharmacokinetics, i.e. to monitor the level of very active drugs in patient serum. This factor is of special importance for a new generation of drugs which are efficient in the treatment of AIDS (AZT), cancer (cis-platinate) and immunosuppressants. These drugs are highly toxic and must be used in minimal quantities which are both patient and time of treatment dependent. The continued monitoring of the level of these drugs in the blood is essential, and the objective assessment of an individual's response to chemotherapy including patient compliance with prescribed doses, are essential. In some cases the drug levels in physiological fluids varies too fast, and multiphoton detection enhanced chromatography of human hair is preferred.

Detection of Substances of Abuse

Ultra-sensitivity and specificity are necessary to detect and analyze drugs of abuse. For example, forensic toxicologists have serious difficulties trying to distinguish between heroin use and the use of some opiates such as morphine, codeine and poppy seed food. It is very important to be able to identify a unique metabolite of heroin: 6-acetylmorphine. However, 6-acetylmorphine has a very short life time in urine (12 h). Therefore, extraction of human hair and subsequent detection of opiates and their metabolites have been studied. H. Gleispach et al., *J. Chromatogr.*, 665, 155, 1994. Since only a very small amount of drug is residual in hair, HPLC/multiphoton detection and TLC/multiphoton detection technology seems to be an ideal candidate for these type of measurements. The same methodology should find numerous applications in sports drug tests for anabolic steroids.

Environmental Applications

Global environmental concerns have created widespread interest in measuring and controlling the environmental impact of industrial and medical waste. However, there are few portable (or transportable) measuring instruments. TLC/multiphoton detection provides an ultrasensitive quantitative analytical system for use in environmental diagnostics, and may permit micro-instrumentation that is backpackable and/or fits into a briefcase.

Two principal areas of application are quantitation of environmental pollutants and tracer studies (TS). The capacity of multiphoton detection to perform quantitation under the environmental background provides unique opportunities for geographic tracer studies. For the mapping of chemical flows through the environment, labeled tracer molecules will constitute only a minuscule contribution to the normal background.

Studies of contamination with pesticides are an important part of environmental diagnostics. In these studies the use of chromatography is very popular, but typically very expensive GC/MS devices are used. Portable TLC/multiphoton detection devices can replace more costly, laboratory based modalities. Considerable economies are expected due to use of higher sensitivity, lower cost devices, higher throughput and lower cost of manpower.

Another important application is the detection of heavy metal ions in water or other fluids. Multiphoton detection enhanced chromatographic systems according to this invention can be used to separate and quantitate reliably and with excellent sensitivity mixtures consisting of various cations such as Co, Ni, Fe (II), Cd, Mn, Cu, Pb, Zn. TLC modality due to its inherent portability and low cost is a preferred implementation. The post-column derivatizing agent may be radio-iodinated 4-(2-pyridylazo)resorcinol.

Agriculture and Food Products Applications

Another important application is in toxicological diagnostics, i.e. testing of food for contamination with toxins. Current methods have many "holes." There are substances for which the limit of detection by current assays is higher than the concentration which is toxic to humans. For example, this is the case of many aflatoxins. Amino acids are natural compounds of different food products, which through fermentation or spoilage may produce corresponding amines, i.e. biogenic amines are indicators of food quality. Therefore, it is important to determine the ratios of certain biogenic amines to amino acids in different food matrices. Studies of these amines have produced encouraging data and suggest broad applications of multiphoton detection enhanced chromatography in food quality control. The methods of the invention are important for the analysis of agricultural products for pesticides, fungicides and decomposition products.

Industrial Applications

Analytical technologies are extensively used by pharmaceutical, petroleum and synthetic chemistry. The characteristic sample makeup in these industries is a mix of as many as a few dozen components, with some important contamination with molecular weights in the range of 200 to 1000 daltons. J. R. Voelker et al., *Clin. Chem.* 40, 1537, 1993. The use of chromatography in such analysis is a mature technique, especially since the main issue is often not only sensitivity but also specificity, i.e. ability to detect the contaminant in the presence of chemical analogs which may be billions of times more abundant.

The problem of spills is increasingly important in the petroleum and chemical industries. Using multiphoton detection one can study the propagation of hydrocarbons in the soil. Also, in an increasing number of cases current techniques are unable to find the sources of hydrocarbons spills. Actually, the contamination of sea by petroleum spills is mostly due to small losses, including the cleaning of bunkers. These "mini spills" lead to very fast spreading and it is often difficult to trace the culprit due to the very high dilution of released material. Tracer methodology permits reliable tracing of spill amount and origin.

Detection of Explosives

Portable multiphoton detection enhanced chromatographic detectors permit measurement of sub-femtomole levels of vapors and aerosols of explosives. at sub-pg/ml concentrations, where both the reliability and specificity of detection are crucial. Detection and quantitation of sub-picomole amounts of explosives and their degradation products is of tremendous importance to aviation safety, and to decrease the clean-up and disposal costs in such industries as mining, construction, chemical industry and military arms factories. HPLC/multiphoton detection and TLC/multiphoton detection may permit fast and reliable screening of luggage before it is loaded on the plane at civilian airports. Also, sensitive detection of unexploded ordinance from past armed conflicts is very important. Effective methods of detection of explosives and their degradation products can prevent accidents, which have been common in the mine fields from previous wars.

Since several compounds are used as explosives and they can form many degradation products, it is not surprising that the most often used analytical technique is chromatography. H. Tabei et al., *Anal Chem.* 66, 3500, 1994. The use of chromatography is facilitated by the fact that most of the nitroaromatics or nitramines are small molecules. Chromatography has been used extensively for detection of explosives, e.g through the quantitation of UV absorption in traces of amines and nitro compounds. M. E. Bovingdon, R. A. Webster, *J. Chromatogr.* B 659, 157, 1994. It is currently the only methodology which can measure simultaneously and reliably various explosives at low abundance.

Existing air collecting devices can be used because the sensitivity of HPLC/multiphoton detection and TLC/multiphoton detection is much higher than the equivalent partial pressure of explosives at room temperature. Therefore, one can collect air using a sniffing device and then submit the collected mixture (potentially containing vapors from explosives) to reduction, derivatization and chromatographic separation using multiphoton detection. Practically all contemporary explosives belong to nitro compounds. Multiphoton detection enhanced chromatographic technique for detection of explosives comprises the steps of: reduction, derivatization of resulting amines, hydrazines or alcohols, and subsequent multiphoton detection enhanced chromatography.

Explosives in use today contain several nitro groups. J.A.D.M. Tonnaer, "Angiotensins", in *Handbook of HPLC for separation of Amino Acids, Peptides and Proteins* Vol. II. p. 179, 1984; C. Steuckart, E. Berger-Preiss, K. Levsen, *Anal Chem.* 66, 2570, 1994; and W. H. Church, et al., *Advances in Chromatography,* V., 128, Marcel Dekker, NY, p. 165, 1989. Nitro groups, after reduction to amines, hydrazines or alcohols., can be easily derivatized with multiphoton detection compatible radio-isotopes. The use of HPLC/multiphoton detection and TLC/multiphoton detection permits higher sensitivity and more reliable quantitation.

Reduction

With explosives and in other applications, prior to derivatizing, it may be helpful to reduce components of a mixture. Reducing methods can be divided into three groups:

1. Catalyzed (homogenous or heterogenous) hydrogenation.
2. Metals in acidic solutions.
3. Chemical reducing agents such as lithium aluminum hydride ($LiAlH_4$), sodium borohydride ($NaBH_4$) and its sulfurized analog ($NaBS_2H_4$) etc.

As to (2), one possibility is the use of zinc in hydrochloric acid solutions (possibly in anhydrous conditions to facilitate subsequent derivatization), or magnesium in ammonium sulfate solution. The reactions are tested using model compounds: nitrophenol (acid) and nitroaniline (base). It is also possible to combine solubilization and reduction by pumping a gaseous sample through a reducing solution (possibly through a membrane filter, e.g. 0.22 microns PTFE or Nylon with luer fitting). Reduction in acidic conditions results in an ionic ammonium salt, which can be efficiently removed from the gas, easily filtered to separate it from the excess of the metal, and extracted from the reduction mixture or subjected to derivatization reaction without purification, possibly after immobilization on the column. Also, chromatography is typically more reliable than prior-art immunoassays when the presence of degradation or decomposition products provide artifactual receptors to antibodies.

Derivatization Techniques for Multiphoton Detection Enhanced Chromatography.

The derivatization techniques applicable to multiphoton detection enhanced chromatography depend on both the application and on the chemistry of the radio-isotopes used. The derivatization can take place either on-line or off-line and either before or after the separation step.

Preferably, the radioemitters belong to the family of electron capture (EC) emitters and/or positron-gamma (pg) radio-emitters. More specifically, the emitter may belong to:

the family of halogens, including bromine and iodine, e.g. $Br^{76}$(16.5 h), $Br^{77}$(2.6 d); $I^{123}$(10 h), $I^{124}$(4.2 d), $I^{125}$(60 d), $I126$(13.2 d);

the family of lanthanides, including $La^{135}$(19.8 h); $Ce^{133}$ (6.3 h), $Ce^{134}$(3.0 d), $Ce^{135}$(22.0 h), $Ce^{137}$(9.0 h), $Ce^{139}$(140 d); $Nd^{140}$(3.3 d); $Pm^{143}$(265 d), $Pm^{144}$ (440 d), $Pm^{145}$(18 y), $Pm^{146}$(710 d), $Pm^{158m}$(40.6 d); $Sm^{145}$ (340 d); $Eu^{145}$(5.6 d), $Eu^{146m}$(1.58 d), $Eu^{146}$(4.6 d), $Eu^{147}$(24 d), $Eu^{148}$(54 d), $Eu^{149}$(120 d), $Eu^{150m}$(14 h), $Eu^{150}$ (5 y) $Eu^{152}$ (13 y); $Gd^{146}$(48 d), $Gd^{147}$(35 h), $Gd^{149}$(9 d), $Gd^{151}$(120 d), $Gd^{153}$(200 d); $Tb^{151}$(19 h), $Tb^{152}$(18 h), $Tb^{153}$(2.58 d), $Tb^{154m}$(8 h), $Tb^{154}$(21 h), $Tb^{165}$(5.4 d), $Tb^{160}$(73 d); $Dy^{155}$(10 h), $Dy^{157}$(8.2 h); $Tm^{165}$(1.21 d), $Tm^{167}$(9.6 d), $Tm^{168}$(85 d); $Yb^{169}$(32 d); $Lu^{169}$(1.5 d), $Lu^{170}$(2.0 d), $Lu^{171}$ (8.3 d), $Lu^{172}$(6.7 d), $Lu^{173}$(1.3 y), $Lu^{174m}$(165 d); $Hf^{173}$(24 h), $Hf^{175}$(70 d); $Ta^{175}$(11 h), $Ta^{176}$(8.0 h), $Ta^{177}$(2.21 d), $Ta^{179}$(1.6 y), $Ta^{180m}$(8.1 h).

the family of heavy metals, including $W^{181}$(130 d); $Re^{181}$ (20 h), $Re^{182\ m}$(13 h), $Re^{182}$(64 h), $Re^{183}$(71 d), $Re^{184m}$(2.2 d), $Re^{184}$(50 d), $Re^{186}$(90 h); $Os^{183m}$(10 h), $OS^{183}$(12 h), $Os^{185}$(94 d), $Ir^{185}$(15 h), $Ir^{187}$(12 h), $Ir^{188}$(1.71 d), $Ir^{189}$(11 d), $Ir^{190}$(11 d), $Ir^{192}$(74 d); $Pt^{191}$ (3.0 d); $Au^{193}$(15.8 h), $Au^{194}$(39 h), $Au^{195}$ (200 d), $Au^{196}$(5.55 d); $Hg^{193m}$(1.1 d), $Hg^{193}$(6 h), $Hg^{194}$(130 d), $Hg^{195}$(1.66 d), $Hg^{195}$(9.5 h), $Hg^{197m}$(24 h), $Hg^{197}$ (2.71 d); $Tl^{200}$(1.08 d), $Tl^{201}$(3.04 d), $Tl^{202}$(12 d), $Tl^{204}$(3.9 y); $Pb^{200}$(21 h), $Pb^{201}$(9.4 h), $Pb^{202}$(2.17 d); $Bi^{203}$(12.3 h), $Bi^{204}$(11.6 h), $Bi^{206\ m}$(15.3 d), $Bi^{206}$(6.3 d), $Bi^{207}$(30 y);

the family of actinides, including $Po^{206}$(8.8 d); $At^{210}$(8.3 h), $At^{211}$(7.2 h); $Rn^{211}$(16 h), $Ac^{226}$(29 h); $Pa^{228}$(22 h), $Pa^{229}$(1.5 d); $U^{231}$(4.2 d); $Np^{234}$(4.4 d); $Pu^{234}$(9 h), $Pu^{237}$(45.6 d); $Am^{239}$(12 h); $Cm^{241}$(35 d); $Bk^{245}$(4.95 d), $Bk^{246}$(1.8 d).

A particularly useful radio-isotope is iodine-125. It has been long used in medical diagnostics, and the organic chemistry of compounds containing iodine is particularly well established. It is particularly convenient to use radiophores in which the iodine atoms are covalently attached to an aromatic ring. There are several ways of introducing radioactive iodine into the aromatic ring of the derivatizing agent:

modified Sandmeyer reaction of aromatic amines;

intermediate introduction of iodine via electrophilic substitution;

modified Hunsdiecker reaction and/or its modifications;

replacement of carbon-metal bond in thallium, mercury and tin metalloaromatics with radio-iodine;

nucleophilic aromatic substitution of halides in the presence of Cu(I) salts.

Similar methods can be used to introduce EC isotopes from the family of bromine isotopes. However, the richest family of EC isotopes are the lanthanides.

The methods for incorporating EC isotopes into some important organic materials have in common the following:

(1) The practicability of a given method of radio-labeling is strongly dependent on the available quantity of material to be labeled. Techniques for picomole levels are not generally applicable to permit sub-femtomole sensitivity.

(2) Non-specific biological background may present problems, especially when one attempts to detect/quantify ultra-low concentrations in physiological fluids. For example, the dynamic range of the abundance of structurally similar peptides may be between an attomole/ml and sub-nanomole/ml.

(3) Classical methods used for introducing radioiodine or compounds containing radio-iodine for radioimmunoassys are not practical for derivatization for multiphoton detection enhanced radio-chromatography. Appropriate modifications can often be counter-intuitive. For example, the conjugation methods for production of labeled antibodies or antigens are not critically limited by conjugation time. In pre-column derivatization for chromatography, however, the time of derivatization should be much shorter than the typical time of column separation, which is about 30 minutes but may be as short as a few minutes. Furthermore, the typical medium for radio-labeling used in other techniques is water. Derivatization developed for multiphoton detection enhanced chromatography often uses solvents other than water. In some cases, when palladium compounds are used even traces of water drastically diminish the derivatization efficiency.

(4) Temperature and pH are important parameters in radio-labeling procedures, but also influence the chromatographic resolution. The disclosed pre-column derivatization protocols have been optimized to take into consideration this trade-off;

(5) For classical radio-iodination, e.g. Sandmeyer reaction, the incorporation of radio-iodine is both much less efficient and much less reproducible than incorporation of "cold" iodine. To avoid this problem, one can use a two step protocol in which the first step uses "cold" iodine. In the second step, there is isotopic replacement and radio-iodine is introduced.

The following provides details of the synthetic design leading to the synthesis of iodo-radiophores for particularly important functional groups.

Amino Group (Amines, Amino Acids, Peptides, Proteins, Alkaloids).

Iodinated Bolton-Hunter Reagent

Bolton-Hunter reagent is the only commercially available radiophore compatible with certain aspects of multiphoton detection enhanced chromatography. It is used to introduce radio-iodine atoms into molecules of peptides but it can be applied to any compounds containing a primary amino group. The presence of a hydroxyl group on the aromatic ring makes this compound an undesirable derivatizing agent, however.

Iodophthalaldehyde (Iodo-OPA)

For quantitation of amines, amino acids and peptides phthalaldehyde is particularly attractive since it reacts with a large class of important compounds, and the multiphoton detection tracer can be efficiently introduced. Additionally, o-phthalaldehyde is an excellent reagent for derivatization of thiols, primary aminos, amino acids. Synthesis of the binding agent is accomplished as follows: first, 4-nitro- or 4-aminophthalic acid is reduced with lithium aluminum hydride to the aminodiol. The reduction, after hydrolysis, is followed by exhaustive extraction of the reaction mixture with THF to yield aminodiol. Subsequent reactions with nitrous acid and with sodium iodide ($NaI^{125}$) in the presence of powdered copper and ultra-sound yield the iodinated product which is then oxidized with pyridinium chlorochromate to give the 4-$I^{125}$-iodophthalaldehyde. Higher yield can be achieved when the modified Sandmeyer reaction is carried out with non-radioactive iodide and the product is reacted, first with hexabutylditin and tetrakis (triphenylphosphine)palladium(0), and then with sodium iodide ($NaI^{125}$) in the presence of the oxidizing agent.

Pipsyl Chloride

The radioactive version of pipsyl chloride was synthesized from the p-aminobenzenesulfonic acid which was reacted first, with formed in situ nitrous acid to give diazonium salt, which was then reacted with the iodide ions. The pipsic acid which was formed was subsequently reacted with such reagents as phosphorus oxychloride or thionyl chloride to give p-iodobenzenesulfonyl chloride (pipsyl chloride). It Pipsyl chloride can also be used as the derivatizing agent for alcohol and hydrazine functionalities. The "cold" pipsyl chloride is commercially available, which facilitates all the optimization processes, such as optimization of derivatization conditions and of separation conditions.

Hydroxy Group (Alcohols, Carbohydrates, Several Steroids, Prostaglandins)

p-Iodobenzoyl Chloride

The starting reactant is non-radioactive ethyl bromobenzoate. This compound is reacted first in dry dioxane with hexamethylditin (or hexa-n-butylditin) in the presence of tetrakis (triphenylphosphine)palladium(0) to give the trimethyltin (tributyltin) derivative which is treated with $NaI^{125}$ and Chloramine-T to give the desired radio-iodo product. Next, this radioactive ester is chromatographed, hydrolyzed with lithium hydroxide in THF and reacted with thionyl chloride or phosphorus pentachloride to yield the desired radio-iodo benzoyl chloride. This radiophore can be also applied to derivatization of amines.

Carbonyl Group (Aldehydes, Ketones, Some Steroids).

p-Iodophenylhydrazine (PIPH)

The starting reactant is phenylhydrazine. The hydrazine group is protected, the aromatic ring is nitrated and subsequently, the nitro-product is chromatographed, reduced to amine, reacted with nitrous acid and sodium iodide to give p-iodo-substituted protected phenylhydrazine. Subsequently it is reacted with hexabutylditin and tetrakis (triphenylphosphine)palladium(0) and then with sodium iodide ($NaI^{125}$) in the presence of such oxidizing agent as Chloramine-T. The final step, deprotection, gives p-$I^{125}$-iodophenylhydrazine.

Catechol Functionality 1,2-di(p-iodophenyl)ethylenediamine

Several neurotransmitters contain two hydroxy groups in ortho position of the benzene ring. 1,2-diphenylethylenediamine is a very specific derivatizing agent for catechols and catecholamines. The starting material for the synthesis of the radio-iodo analog is p-bromobenzaldehyde. The benzoin reaction in the presence of cyanide ions gives racemic p-bromobenzoin, which is oxidized with chromium oxide in pyridine to non-chiral p-bromobenzil. This compound is reacted either with copper (monovalent) $I^{125}$-iodide in glacial acetic acid (150° C.) or with hexabutylditin and tetrakis (triphenylphosphine) palladium(0) and then with sodium iodide ($NaI^{125}$) to yield radioactive p-iodobenzil. The formation of dioxime with hydroxylamine and subsequent reduction gives the desired 1,2-di(p-$I^{125}$-iodophenyl)ethylenediamine.

The purpose of disclosing the above synthetic designs is not to limit the scope of the invention but rather to show some of the synthetic routes to different derivatizing agents. As is often in the case organic synthetic practice, all of these methods can be implemented using various detailed procedures. There are several synthetic methods which can be applied to synthesis of desired radiophores and therefore, the above descriptions should serve only as examples.

The synthesized radiophores can be used for derivatization of appropriate functional groups as indicated. Due to diverse characteristics of the compounds having such functional groups and also due to the extremely small amounts required for detection by multiphoton detection, some special adjustment of multiphoton emitter enhanced chromatography may be necessary.

Derivatization with Radiophores Containing Lanthanides and Heavy Metals

Lanthanides are particularly attractive for multiphoton detection detection. More than 30 different lanthanide isotopes show the appropriate decay pattern for use in multiphoton detection. Thus, several distinguishable isotopes with very similar chemical properties can be used at the same time. Also, luminescent complexes of lanthanides such as cryptate complexes of lanthanides are known and biologically active compounds with attached cryptate moiety can be synthesized. Also, the biochemistry of conjugating lanthanides to oligonucleotides has been studied. Europium containing compounds are applicable to chromatographic derivatization. Also, according to the invention, the appropriate derivatives of ethylenediaminetetraacetic acid or diethylenetriaminetetraacetic acid may be complexed to radioactive isotopes of lanthanides such as europium ($Eu^{3+}$) (radio-europium chelates) are reacted with amines, alcohols or thiols.

Post-Column Derivatization

For some applications post-column conjugation may be preferable or even necessary. The derivatizing agent(s) is used at the end of the chromatographic column, shifting chemistry from pre-column to post-column techniques. In particular, one can derivatize 2 D outputs of the fractionation process (chromatographic blots). Thus, many limitations of pre-column derivatization techniques can be removed. For example, to increase efficiency, the derivatization time can be longer than the separation time. Also, multi-step derivatization processes with each step at different temperature and pH are clearly feasible. In all post-column derivatizations the non-specific backgrounds should be considered and may be a limiting factor.

Derivatization Techniques for Biomedical Applications

Neurotransmitters (amines, catecholamines), steroids (belonging to alcohols and/or ketones), angiotensins (amines), and other biomolecules can be pre/post fractionation derivatized by reaction of the specific functionality with derivatizing agents containing radiolabels. In the selection of an appropriate derivatizing agent one has to take into account the availability of starting materials, reliability, cost and the need for only one iodo-isomer to be formed in a given synthetic step.

Derivatizing agents containing multiphoton emitting radioisotopes may be used to introduce multiphoton detection compatible radioactive properties into the mixtures separated by chromatography. The majority of derivatization techniques involve radioiodination wherein the functionality of the derivatizing agent is such as to:

form amides with amines;

form carbamates or thiocarbamates with amines;

form substituted isoindole with amino group in the presence of appropriate thiols;

form esters with alcohols;

form phenylhydrazones with aldehydes and ketones;

form substituted oxazoles with catechols and catecholamines.

More specifically, radiophores are applicable to separation, detection and quantitation of:

amines, amino acids, peptides such as angiotensins, proteins;

alcohols such as saccharides;

alcohols and ketones belonging to steroids or prostaglandins;

mixtures containing anions;

mixtures containing cations.

Other Applications of Derivatization Using Radiophores

Nitro Group (Explosives)

There are no good derivatizing agents for the nitro group, but all the reduction products of explosives can be derivatized. The explosives in current use can be divided to the following categories:

nitroaromatics, where the nitrogen atom of the nitro group is attached to the carbon atom of the aromatic ring. Compounds such as TNT (2,4,6-trinitrotoluene), picric acid (2,4,6-trinitrophenol), DNTs (isomeric dinitrotoluenes) and hexyl (2,2',4,4', 6,6'-hexanitrodiphenylamine) belong to this class. Nitrotoluenes, and especially trinitrotoluenes, are highly toxic compounds.

nitramines, such as RDX (1,3,5-trinitro-1,3,5-triazacyclohexane) and HMX (1,3,5,7-tetranitro-1,3,5,7-tetraazacyclooctane) are compounds in which the nitrogen atom of the nitro group is bonded to the nitrogen atom of the amino group. Explosives belonging to the newest generation such as CL-20 and TNAZ belong to this class.

esters of nitric acid, in which the nitrogen atom of the nitro group is attached to the oxygen atom. Such compounds as EGDN (ethylene glycol dinitrate), PETN (pentaerythritol tetranitrate), NG (glycerol trinitrate, popularly but incorrectly called nitroglycerine) and cellulose trinitrate (called nitrocellulose even if nitration of cellulose is not complete) are in this class.

mixed compounds, in which two types of $NO_2$ group bonding take place. Tetryl (2,4,6,N-tetranitro-N-methylaniline) is an example of such explosive.

Thus, the most common functionality in explosives is a nitro-group. The separation of explosives and their degradation products can be preceded by a process in which all the aromatic nitro-groups are reduced to aromatic amino groups, nitramines are reduced to hydrazines and esters of nitric acid are hydrolyzed to alcohols. $I^{125}$-Pipsyl chloride can be used for derivatization of all these reduction products.

Phthalaldehyde (OPA) is an excellent derivatizing agent for primary amines. Therefore, one may also employ the radio-analog of this reagent. A preferred alternative is phenyl isocyanate. The radiophore can be synthesized starting from commercially available 4-methoxyphenyl isocyanate. Radio-iodination with an excess of sodium iodide-125 in the presence of Chloramine T or similarly acting oxidizing agent gives 4-methoxy-3,5-di-($I^{125}$)iodophenyl isocyanate radiophore for amines. Reduction of some explosive materials gives oligohydroxy products, which may be reacted with a labeled derivatizing agent for alcohols, such as $^{125}I$-iodonitrobenzoyl chloride and similar compounds discussed above.

A technique for separation of a mixture of selected simple aromatic amines and a mixture of simple oligohydroxy compounds like glycerol and pentaerythritol is as follows: A mixture of several potential explosives and related compounds is submitted, first to reduction and then to on line derivatization (with both reagents) and chromatographic separation. The reducing agent can be attached to a solid support so that the mixture is submitted to one column only. This column may consist of a preliminary purification area, reducing agent area, radioderivatization area, separation area and detection area. In some cases it may contain an amines removal area at the top of the column. That way, the time of analysis may be diminished dramatically. To prevent false negatives and false positives it may be important to perform chromatography of the unreduced mixture as well.

Multiphoton detection enhanced chromatographic systems facilitate separation of mixtures consisting of different nitro compounds present in explosives which are first reduced and then chromatographed with pre- or post- column derivatization with appropriate radiophore such as $I^{125}$-pipsyl chloride and detection using multiphoton detection. If components of the mixture also contain functionalities which are the same as reduction products, the derivatization of the mixture, separation and quantitation preferably takes place before the reduction of a sample. Quantitation of reduced and non-reduced mixture provides data sufficient for quantitation of all the nitro compounds present in the mixture. For example, for nitro compounds which belong to the explosives, reduction is followed by derivatization of the formed poly-amines, poly-hydrazines and poly-alcohols with appropriate radiophore such as $I^{125}$ pipsyl chloride, followed by chromatography and detection of the separate fractions using multiphoton detection.

Drugs of Abuse

There are five main groups of drugs of abuse (amphetamines, cocaine and metabolites, opiates, phencyclidines and cannabinoids). The first four groups are amines. Since some of them are tertiary amines post-column derivatization is the method of choice. Pipsic acid is a particularly good derivatizing agent which forms salts with tertiary as well as primary and secondary amines. Additionally, post-derivatization with a radiophore for the hydroxyl group (such as benzoyl chloride) of cannabinoids has to be used. After removal of the excess derivatizing agent, fractions are submitted to multiphoton detection detection and quantitation.

Multiphoton detection enhanced chromatographic techniques can facilitate the detection of drugs of abuse. A sample of the air is obtained using commercially available "sniffers". It is trapped into a wet filter with affinity for drugs. Alternatively, appropriate molecular sieves can be used. The liquid can then be fractionated by a plurality of chromatographic techniques, e.g. GC/multiphoton detection, HPLC/multiphoton detection and TLC/multiphoton detection. Of course, contaminated air (breath) is not the only source of samples suspected to contain drugs of abuse. We expect to use multiphoton detection/chromatography to detect drugs in samples of serum, urine, hair, saliva and so on.

Tagging of petrochemical products: To identify the source of different petroleum and chemical mixtures, various liquid cargoes should be tagged, for example using a particular set of steroids or terpenes or similar compounds. A given cargo is tagged with an ultra small amount of a few compounds chosen from a predetermined set of convenient compounds. In case of a spill, a sample can be taken to the laboratory, derivatized with appropriate agent for the given functionality, chromatographed under preestablished conditions and quantitated with multiphoton detection. Optionally, all the chemistry can be performed at the place of the spill and a portable multiphoton detection can be used to quantitate the fractionation output.

Alternatively, a petrochemical cargo can be labeled with sodium radio-iodide or other appropriate salts containing radio elements compatible with multiphoton detection with complexing agents such as functionalized crown ethers to provide solubility. The presence of the radio-isotope identifies the cargo as tagged. In case of need the functionalized crown ether can be derivatized, chromatographed and detected using multiphoton detection. These methods enable introduction of the equivalent of "bar coding" to almost all liquid products. Multiphoton detection enhanced chromatography makes possible the use of economically and environmentally reasonable amounts of labeling chemicals.

A particular application of multiphoton detection enhanced chromatographic systems is in the petroleum industry. One of the tasks is to measure the spills of hydrocarbons from storage vessels, tankers and pipelines. One may add a negligible amount of an EC tag to a large amount of fluids; economical considerations suggest that the minimal dilution should be 1 part per billion (1 PCB). Appropriately EC tagged organic compounds soluble in hydrocarbons may be used. To provide a very large family of such radio-tagged compounds. This permits the capability of introducing a "chemical bar-code" into each shipment of petroleum and/or bulk chemicals.

Phase transfer catalysts such as crown ethers, corronands, cryptands, tetraalkylammonium salts, tetraalkylphosphonium salts and similar compounds permit solubilization of radioactive sodium or potassium iodide or other radioelements compatible with multiphoton detection and thus permit labelling of hydrocarbon mixtures such as crude oil, gasoline and other petrochemical products. After chromatographic fractionation the labeled mixtures are quantitated using multiphoton detection. Also, mixtures containing crown ethers, cryptands and similar complexing agents can be easily post-separation derivatized; ie. the step of detection by multiphoton detection is preceded with treatment of samples with salts of $I^{125}$ iodide anion.

Also, other large groups of organic or biological products are well soluble in hydrocarbons. Thus, the use of terpenes, steroids and similar compounds containing appropriate functional groups for introducing a unique signature to different cargos is desirable. The set of a few tens of individual compounds comprises a unique fingerprint for a given product and the origin of an unknown sample (spill) can be easily determined. Radio-derivatization of the signature compound followed by multiphoton detection enhanced chromatography enables distinguishing among many different possibilities. The high sensitivity of multiphoton detection is essential to achieve the benefit of using as small amounts of tagging compounds as possible.

Particular $I^{125}$ Derivatizing Agents

The derivatizing agent may be a monofunctional reagent specific for a class of compounds, e.g. amines, and is reacted with the components of the mixture prior to submitting the mixture to separation on the chromatographic column. This approach is appropriate for the great majority of biological applications of multiphoton detection enhanced chromatography.

For the quantitation of amines, amino acids and peptides, phthalaldehyde is particularly attractive since it reacts with a large class of important compounds, and the multiphoton detection tracer can be easily introduced. Additionally, o-phthalaldehyde is an excellent reagent for derivatization of thiols. Pipsyl chloride is another derivatizing agent for the amino group. The radioactive version has been synthesized from the p-aminobenzenesulfonic acid which was reacted with radio-iodide via diazonium salt. The product is then reacted with phosphorus oxychloride. Pipsyl chloride, being a sulfonyl chloride, is also a derivatizing agent for alcohols.

Due to the presence of many precursors and metabolites, the measurement of catecholamines in biological samples requires particularly high selectivity and sensitivity. The reagents for general amino compounds do not have sufficient selectivity for this purpose. However, 1,2-diphenylethylenediamine (DPE) is a highly selective reagent for catecholamines. It takes advantage of the presence of two phenolic hydroxyl groups in ortho position in the aromatic ring. Since the compound contains two aromatic rings it is relatively easy to synthesize the radio-labeled 1,2-diphenylethylenediamine.

The disclosed synthesis starts with commercially available 4-nitrobenzaldehyde. Careful reduction of the nitro group gives the aromatic amine. The reaction with nitrous acid followed by addition of sodium iodide produces the p-iodo-derivative. This compound is then submitted to benzoin reaction in the presence of cyanide anions. Labeled benzoin is thus oxidized to diketone, reacted with hydroxylamine to give the oxime and finally reduced to diamine. Then, the meso product is separated by column chromatography from the racemic mixture. The proposed synthesis is one of many possible synthetic approaches. Other variants permit optimized synthesis starting from non-radioactive (cold) material. One of the advantages of this methodology is the fact that if commercially available dinitrobenzaldehyde is the synthesis substrate, the final product has twice the number of iodine atoms in one molecule of derivatizing agent. This translates to doubled sensitivity of this agent in multiphoton detection enhanced chromatography.

Meso-1,2-bis(4-methoxyphenyl) ethylenediamine is an excellent starting material for the synthesis of a radiophore for the catechol group. Electrophilic aromatic substitution with radio-iodine (iodide plus oxidizing agent such as Chloramine T) followed by preparative HPLC gives tetraiodo compound in good yield.

Many steroids, particularly those present in physiological fluids, contain one or more hydroxy groups. Acid chlorides are the reagents of choice for alcohols. The synthesis of the tagged agent can start with commercially available 3,5-dinitrobenzoic acid. Reduction of one of the nitro groups followed by the reaction with nitrous acid (formed in situ) and sodium iodide gives the desired $3-^{125}$-iodo-5-nitrobenzoic acid. 125-Iodonitrobenzoyl chloride is the final product of this reaction sequence. Being a derivatizing agent for the alcohol functionality, it forms derivatives with most steroids of interest. Another synthetic option is radio-iodination of commercially available p-methoxybenzoyl chloride to give 3,5-di($I^{125}$)iodo-4-m ethoxybenzoyl chloride.

In the separation of mixtures of neurotransmitters containing no radioactive labels, the separation step is made difficult by the presence of a large number of agonists, antagonists and metabolites. Thus, very efficient and specific derivatizing agents for neurotransmitters containing radio-iodine must be synthesized. The most common functionality in neurotransmitters is a primary amine group. Phthalaldehyde (OPA) is an excellent derivatizing agent for primary amines. Iodo-labeled derivatizing agent for primary amines (iodo-OPA) and for catechols (iodo-DPE) can be applied to the separation and detection of natural mixtures of neurotransmitters even at a concentration of about 10 fg/ml.

A synthesis of radio-iodo-labeled meso-1,2-diphenylethylenediamine (DPE)—a derivatizing agent for catechols and catecholamines—is as follows. The starting reactant is p-bromobenzaldehyde. The benzoin reaction in the presence of cyanide ions gives racemic p-bromobenzoin, which is oxidized with chromium oxide in pyridine to non-chiral p-bromobenzil. This compound is reacted either with copper (monovalent) $I^{125}$-iodide in glacial acetic acid (150° C.) or with hexabutylditin and tetrakis (triphenylphosphine)palladium(0) and then with sodium iodide ($NaI^{125}$) to yield radioactive p-iodobenzil. The formation of dioxime with hydroxylamine and subsequent reduction gives desired 1,2-di(p-$I^{125}$-iodophenyl) ethylenediamine as a mixture of diastereoisomers. Preparative HPLC gives the final meso product.

Another implementation involves synthesis of radio-iodophenylhydrazine—a derivatizing agent for aldehydes and ketones. The starting reactant is phenylhydrazine. The hydrazine group is protected, the aromatic ring is nitrated, reduced to amine, reacted with nitrous acid and sodium iodide to give p-iodo-substituted protected phenylhydrazine. Subsequent reaction with hexabutylditin and tetrakis (triphenylphosphine) palladium(0) and then with sodium iodide ($NaI^{125}$) followed by the deprotection step gives p-$^{125}$I-iodophenylhydrazine.

An alternative derivatizing agent for the carbonyl group is 3,5-di-($I^{125}$)iodo-4-methoxybenzenesulfonyl hydrazide. It was synthesized from non-iodinated analog by reaction with excess of sodium iodide-125 and Chloramine T in ethanol. HPLC showed formation of essentially one product. It was purified by preparative HPLC.

When post-separation derivatization is used the mixture is separated first, and then derivatized with appropriate acid containing radio-isotope such as pipsic acid (p-$I^{125}$-iodobenzenesulfonic acid) to detect amines as bases (amphetamines, cocaine and metabolites, opiates, phencyclidines), and with appropriate radio-labeled derivatizing agent for alcohols such as p-$^{125}$I-iodobenzoyl chloride to detect hydroxyl functionality (cannabinoids). After removal (dissolving or absorbing) of the excess of the derivatizing agent the fractions are submitted to multiphoton detection detection and quantitation.

Another implementation of derivatization for both biomedical diagnostics and drug detection involves the synthesis of radio-iodobenzoyl chloride—a derivatizing agent for amines and alcohols. The starting reactant is non-radioactive ethyl bromobenzoate. This compound is reacted first in dry dioxane with hexamethylditin (or hexa-n-butylditin) in the presence of tetrakis (triphenylphosphine) palladium(0) to give the trimethyltin (tributyltin) derivative which is treated with $NaI^{125}$ and Chloramine-T to give the desired radio-iodo product. Next, this radioactive ester is chromatographed, hydrolyzed with lithium hydroxide in THF and reacted with thionyl chloride or phosphorus pentachloride to yield the radio-iodobenzoyl chloride.

Yet another implementation of derivatization for both biomedical diagnostics and drug detection involves synthesis of radioactive pipsyl chloride—a derivatizing agent for amines and alcohols. The starting reactant is p-aminobenzenesulfonic acid. The sulfanilic acid is dissolved in dioxane and reacted with nitrous acid prepared in situ from sodium nitrite and hydrochloric acid at temperature below 0° C. to produce the diazonium salt. The diazonium salt is then submitted to the modified Sandmeyer reaction conditions i.e. to reaction with sodium iodide ($NaI^{125}$) in the presence of powdered copper and ultrasound. Next, the product—radio-iodinated sulfonic acid—is reacted with phosphorus pentachloride to yield $I^{125}$-pipsyl chloride.

Derivatizing agents may contain two or more multiphoton detection compatible radioactive atoms in one molecule. The use of many radio atoms per one molecule of the derivatizing agent amplifies the signal and improves the already ultra high sensitivity of the chromatography/multiphoton detection method.

Pre-fractionation derivatization may be more complicated than post-fraction derivatization, wherein separation is applied to a mixture containing similar compounds differing significantly in their concentration. The mixture is chromatographed first, using a fraction collector, and next, the fractions containing compounds of interest are treated with a relatively small excess of radio-labeled derivatizing agent. After the derivatization is complete, each of the fractions to which derivatizing agent has been added is treated with beads containing the appropriate functionality to remove the excess derivatizing agent. Quantitation using multiphoton detection takes place after the beads have been filtered off. This methodology enables quantitation of compounds present in the mixture in very small amounts despite the presence of similar but abundant components of the mixture. For example, the first step of pre-separation may be performed using TLC and the second using HPLC. Generically such methods permit higher specificity of the chromatographic process through the use of multi-step separation, wherein either two chromatographic modalities are used or two different chromatographic conditions are used. This leads to some losses of signal; generally, even if signal is lost the signal/background is improved. Fortunately, multiphoton detection enhanced chromatography is sensitive enough to permit a plurality of such steps.

Multicolor Derivatization Using Radio-Iodines and Radio-Bromines

In many cases, even the best chromatographic techniques only partially separate the members of a family of analytes with similar chemical properties, e.g pesticides.

When attempting multicolor chromatography, there is a trade-off between specificity and sensitivity. Typically, the analytes flow through a multilayer derivatization zone, where diverse "tags" are attached to analytes in a cascaded, step-by-step process. Thus all analytes are submitted to all derivatization processes, i.e. there is no loss of sensitivity. However, this means that the time of derivatization is essentially the sum of the times of each of the protocols, which leads to considerably lower throughput. Ever more important are problems of selective derivatization and uncertainties due to competitive derivatization. Often, the diverse derivatization protocols are not compatible, i.e. some can be performed in water wherein others require other solvents. Also, some procedures are not compatible because of different temperatures required. Finally, times of different protocols may be very different, i.e. the efficiency of slower reactions are too low. Often the protocols are not commutative and the results depend on the temporal order of their performance.

All of these complications are minimized if the derivatization processes are performed in parallel, each in its own container/environment. However, this means that for multicolor chromatography having m colors, each derivatization process uses 1/m of the total amount of material to be analyzed. Thus, the selectivity may be increased up to the number of colors employed, but sensitivity diminishes to the same extent. However, the exquisite sensitivity of multiphoton detection enhanced chromatography enables new multicolor and pre-fractionation derivatization techniques to be used.

For example, compounds with a plurality of iodine and bromine isotopes, preferably $I^{123}$, $I^{124}$, $I^{125}$ and $I^{126,}$ and also radio-bromines, may be used first. When using Ge-detectors, due to the negligible width of gamma-ray lines, each isotope can be reliably identified without any crosstalk. Second, multiphoton detection enhanced chromatography is superbly sensitive. Thus, a simple "concurrent" derivatization technique can be used. Thus, the analytes to be studied are divided into several parallel micro-capillaries filled with appropriate derivatizing agent. Each microcapillary uses one EC radioisotope. After derivatization, the products are pooled and injected into the chromatographic column for separation and subsequent detection.

The CGX emitter may also be coupled to a monoclonal or polyclonal antibody or an antigen, and the antibody or antigen can be used in an assay. For example, an antibody can be used to detect cancerous cells in a physiological sample. The level of estrogen and other steroids may be used to diagnose breast cancer.

The CGX emitter may be coupled to a unicellular organism such as a virus, a bacterial cell, an algae cell, a fungal cell, or a protozoa. The virus may be an agent of sexually or blood transfusion transmitted disease, and the bacteria may be tubercular bacillus or bacteria which are precursors of sexually transmitted diseases.

The assay may be used to detect contamination of human physiological fluids such as blood, urine, sputum, tear drops, sweat, amniotic fluid or spinal fluid, or animal physiological fluids.

The assay may be used to detect contamination of food and agricultural products, such as the presence of microorganisms and their toxic byproducts, e.g. aflatoxins or mycotoxins. The assay may also be used to detect contamination of samples of water, soil or air from the environment, and chemical contamination such as pesticides, herbicides, PCBs, dioxin, and heavy metals.

The assay can be performed upon airborne substances in a clean room environment, and data are used to estimate the number and size distribution of micron sized dust and other particles suspended in the air.

In recent years multivalent metals have also entered service as labels. They are captured in chelating complexes which are constituents of, or can be adducted to, molecules or macromolecules to be quantitated. In addition the metal scavenging protein metallothionine can capture 20–40 atoms of multivalent metals. Metallothionine has recently been used as a constituent of genetically engineered fusion proteins. Its high carrying capacity is thus coupled, for example, with the targeting specificity of antibodies. A highly selective delivery of label to particular antigenic targets within complex cellular mixtures can thus be achieved.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced otherwise than as specifically described.

What is claimed is:

1. A method for detecting an analyte of interest present in a mixture, comprising the steps of:

selecting a radioactive derivatizing agent comprising a multiphoton-emitting radioisotope and a moiety reactive with the analyte of interest, derivatizing the analyte of interest with the derivatizing agent to form a derivative by allowing the moiety reactive with the analyte of interest to form a non-covalent chemical bond with the analyte of interest;

without regard to order as to the derivatizing step, separating the mixture into fractions by chromatography; and detecting the derivatized analyte of interest in at least one of the fractions using multiphoton detection.

2. The method of claim 1, wherein the derivatizing step is performed after the separating step, and further comprising removing excess non-reacted derivatizing agent prior to the detecting step.

3. The method of claim 2, wherein the removing step comprises adding an affinity reagent that binds non-reacted derivatizing agent and removing the affinity reagent from the derivatized analyte of interest.

4. The method of claim 1, wherein the radioisotope is bound to the derivatizing agent to produce a radioactive derivatizing agent prior to derivatization of the analyte of interest.

5. The method of claim 1, wherein the radioisotope is covalently bound to the derivatizing agent.

6. The method of claim 1, wherein the derivatizing agent reacts specifically with the functional group of the analyte of interest, at high affinity, at picomolar concentrations of the analyte of interest within hours.

7. The method of claim 1, wherein the amount of radioisotope employed in reacting the radioderivatizing agent with the functional group of the analyte of interest is less than about one nanocurie.

8. The method of claim 1, wherein the separating step comprises separating components of a mixture involving differential migration of the components through a medium, based on the physical-chemical characteristics of the components.

9. The method of claim 1, wherein the separating step is chromatography selected from the group consisting of liquid chromatography (LC), thin layer chromatography (TLC), gas chromatography (GC), ion exchange chromatography (IEC), capillary electrophoresis (CE), high performance liquid chromatography (HPLC), gel electrophoresis, and affinity chromatography.

10. The method of claim 1, wherein the separating step is stopped before the detection step.

11. The method of claim 10, wherein the fractions are collected after chromatographic separation using a fraction collector and are then quantitated off-line by a multiphoton detection device.

12. The method of claim 10, wherein the fractions are collected as blots on a one dimensional substrate and the detecting step comprises scanning the blots.

13. The method of claim 10, wherein the fractions are collected as blots on a two dimensional matrix, and the detecting step comprises spatially resolving detection techniques.

14. The method of claim 10, wherein chromatography is stopped prior to elution of the analyte of interest, by stopping solvent flow or switching to a non-desorbing solvent, and the chromatographic medium is scanned by a multiphoton detection device.

15. The method of claim 1, wherein the radioisotope is selected from the group consisting of electron capture (EC) emitters and positron-gamma (pg) radio-emitters.

16. The method of claim 15, wherein the radioisotope is a halogen.

17. The method of claim 15, wherein the radioisotope is a lanthanide selected from the group consisting of $La^{135}$, $Ce^{133}$, $Ce^{134}$, $Ce^{135}$, $Ce^{137}$, $Ce^{139}$, $Nd^{140}$, $Pm^{143}$, $Pm^{144}$, $Pm^{145}$, $Pm^{146}$, $Pm^{158m}$, $Sm^{145}$, $Eu^{145}$, $Eu^{146}$, $Eu^{147}$, $Eu^{148}$, $Eu^{149}$, $Eu^{150m}$, $Eu^{150}$, $Eu^{152}$, $Gd^{146}$, $Gd^{147}$, $Gd^{149}$, $Gd^{151}$, $Gd^{153}$, $Tb^{151}$, $Tb^{152}$, $Tb^{153}$, $Tb^{154m}$, $Tb^{154}$, $Tb^{165}$, $Tb^{160}$, $Dy^{155}$, $Dy^{157}$, $Tm^{165}$, $Tm^{167}$, $Tm^{168}$, $Yb^{169}$, $Lu^{169}$, $Lu^{170}$, $Lu^{171}$, $Lu^{172}$, $Lu^{173}$, $Lu^{174m}$, $Hf^{173}$, $HF^{175}$, $Ta^{175}$, $Ta^{176}$, $Ta^{177}$, $Ta^{179}$, and $Ta^{180m}$.

18. The method of claim 1, further comprising selecting a plurality of analytes of interest to produce a set of tagging compounds; adding a pre-established signature combination selected from the set of tagging compounds to a bulk mixture to provide a tagged mixture; derivatizing at least one of the tagging compounds with the derivatizing agent; and performing chromatography of the tagged mixture with multiphoton detection.

19. The method of claim 1, wherein the radioactive derivatizing agent is a chelate.

20. The method of claim 1, wherein the reactive moiety of the radioactive derivatizing has an affinity for the analyte of interest.

21. The method of claim 20, wherein the reactive moiety comprises
  (a) where the analyte of interest comprises an antigen, an antibody having an affinity for the antigen of the analyte, or
  (b) where the analyte of interest is an antibody, an antigen or epitope for the antibody of the analyte.

22. The method of claim 1, wherein the analyte of interest contains more than one functionality which can form stable derivatives with the radiophore.

23. The method of claim 2, wherein the mixture contains the analyte of interest and a higher concentration compound having similar reactivity with the derivatizing agent, and further comprising separating the mixture into fractions, treating fractions suspected of containing compounds of interest with a small excess of radiolabeled derivatizing agent to produce derivatized fractions, treating the derivatized fractions with an affinity reagent having the functional group of the analyte of interest to bind excess derivatizing agent, and separating the affinity reagent.

24. The method of claim 3, wherein the affinity reagent is bound to a solid phase component, and separating the affinity reagent is done by filtering or sedimentation.

25. The method of claim 1, comprisings performing thin layer chromatography on a TLC plate having an expected position of the analyte of interest, making a series of windows on the TLC plate at predetermined locations corresponding to the expected position of the analyte of interest, applying the radio-labeled derivatizing agent to the TLC plate through the windows such that derivatization of non-interesting but abundant components of the mixture is avoided, removing the excess derivatizing agent from the plate, and quantitating the presence of derivatized analyte of interest on the TLC plate by multiphoton detection.

26. The method of claim 1, wherein the separation is halted prior to elution of the analyte of interest and the detecting step comprises subjecting the chromatographic medium to multiphoton detection.

27. The method of claim 1, comprising a competitive binding process comprising adding a specified amount of a radioactive derivative of the analyte of interest to a fraction of interest after chromatographic separation where the analyte of interest is expected to be present, treating the fractions of interest with an affinity reagent for the functionality present in the analyte of interest to cause removal of a portion of the radiolabeled derivatizing agent, measuring the radioactivity removed from the fractions of interest, and quantifying the analyte of interest in the fractions of interest.

28. The method of claim 1, wherein a plurality of derivatizing agents are applied to the mixture.

29. The method of claim 28, wherein the derivatizing agents comprise a plurality of agents each having a different colored multiphoton—emitting radioisotope such that different functional groups are derivatized differently.

30. The method of claim 1, wherein the concentration of the analyte of interest in the mixture is high and the radioactive derivatizing agent is mixed with non-radioactive equivalent derivatizing agent prior to the derivatizing step to minimize the amount of radioactivity employed.

31. A method according to claim 1, comprising detecting an analyte of interest present in the mixture at a concentration as low as femtomolar.

32. A method according to claim 1, comprising detecting picogram quantities of the analyte of interest.

33. A method according to claim 1, comprising detecting femtogram quantities of the analyte of interest present in a sample in an amount of femtograms.

34. A method according to claim 1, comprising detecting less than about 50 attomoles of the analyte of interest.

35. A method according to claim 1, comprising detecting an analyte of interest present in the mixture at a concentration of one part per trillion.

36. A method according to claim 1, wherein the amount of radioisotope employed is less than about one picocurie per sample.

37. A method for detecting an analyte of interest in a mixture comprising steps for:
  obtaining a radioactive label comprising a multiphoton-emitting radioisotope and a moiety reactive with the analyte of interest;
  producing a non-covalently labeled analyte of interest using the radioactive label,
  obtaining fractions of the mixture, and
  identifying a fraction of the mixture comprising the labeled analyte of interest.

38. A derivatizing agent comprising a multiphoton-emitting radioisotope and a moiety that forms a non-covalent chemical bond with an analyte of interest, suitable for detection of the analyte of interest by multiphoton detection.

39. The method of claim 1, further comprising without regard to order, removing excess derivatizing agent.

40. A derivatizing agent according to claim 38, wherein the derivatizing agent is a chelate.

41. A derivatizing agent according to claim 38, wherein the derivatizing agent comprises a plurality of agents each having a different colored multiphoton-emitting radioisotope such that different functional groups are derivatized differently.

42. A derivatizing agent according to claim 38, wherein the radioisotope is a positron-gamma (pg) radio-emitter.

43. A derivatizing agent according to claim 38, wherein the radioisotope is a lanthanide selected from the group consisting of $La^{135}$, $Ce^{133}$, $Ce^{134}$, $Ce^{135}$, $Ce^{137}$, $Ce^{139}$, $Nd^{140}$, $PM^{143}$, $Pm^{144}$, $Pm^{145}$, $Pm^{146}$, $Pm^{158m}$, $Sm^{145}$, $Eu^{145}$, $Eu^{146m}$, $Eu^{146}$, $Eu^{147}$, $Eu^{148}$, $Eu^{149}$, $Eu^{150m}$, $Eu^{150}$, $Eu^{152}$, $Gd^{146}$, $Gd^{147}$, $Gd^{149}$, $Gd^{151}$, $Gd^{153}$, $Tb^{151}$, $Tb^{152}$, $Tb^{153}$, $Tb^{154m}$, $Tb^{154}$, $Tb^{165}$, $Tb^{160}$, $Dy^{155}$, $Dy^{157}$, $Tm^{165}$, $Tm^{167}$, $Tm^{168}$, $Yb^{169}$, $Lu^{169}$, $Lu^{170}$, $Lu^{171}$, $Lu^{172}$, $Lu^{173}$, $Lu^{174m}$, $Hf^{173}$, $Hf^{175}$, $Ta^{175}$, $Ta^{176}$, $Ta^{179}$, and $Ta^{180m}$.

44. A derivatizing agent according to claim 38, wherein the radioisotope is a halogen selected from the group consisting of $Br^{76}$, $Br^{77}$, $I^{123}$, $I^{124}$, and $I^{126}$.

45. A derivatizing agent according to claim 38, wherein the radioisotope is an actinide selected from the group consisting of $W^{181}$, $Re^{181}$, $Re^{182m}$, $Re^{182}$, $Re^{183}$, $Re^{184m}$, $Re^{184}$, $Re^{186}$, $Os^{183m}$, $Os^{183}$, $Os^{185}$, $Ir^{185}$, $Ir^{187}$, $Ir^{188}$, $Ir^{189}$, $Ir^{190}$, $Ir^{192}$, $Pt^{191}$, $Au^{193}$, $Au^{194}$, $Au^{195}$, $Au^{196}$, $Hg^{193m}$, $Hg^{193m}$, $Hg^{194}$, $Hg^{195m}$, $Hg^{195}$, $Hg^{197m}$, $Hg^{197}$, $Tl^{200}$, $Tl^{200}$, $Tl^{202}$, $Tl^{204}$, $Pb^{200}$, $Pb^{201}$, $Pb^{202}$, $Bi^{203}$, $B^{204}$, $Bi^{206m}$, $Bi^{206}$, $Bi^{207}$, $Po^{206}$, $At^{210}$, $At^{211}$, $Rn^{211}$, $Ac^{226}$, $Pa^{228}$, $Pa^{229}$, $U^{231}$, $Np^{234}$, $Pu^{234}$, $Pu^{237}$, $Am^{239}$, $Cm^{241}$, $Bk^{245}$, and $Bk^{246}$.

* * * * *